United States Patent
Maggiore

(10) Patent No.: US 8,982,156 B2
(45) Date of Patent: Mar. 17, 2015

(54) ASSEMBLING METHOD, OPERATING METHOD, AUGMENTED REALITY SYSTEM AND COMPUTER PROGRAM PRODUCT

(75) Inventor: Frank Maggiore, Port Jefferson Station, NY (US)

(73) Assignee: Sartorius Stedim Biotech GmbH, Goettingen (DE)

( * ) Notice: Subject to any disclaimer, the term of this patent is extended or adjusted under 35 U.S.C. 154(b) by 219 days.

(21) Appl. No.: 13/643,365

(22) PCT Filed: Apr. 26, 2011

(86) PCT No.: PCT/EP2011/002088
§ 371 (c)(1),
(2), (4) Date: Oct. 25, 2012

(87) PCT Pub. No.: WO2011/154072
PCT Pub. Date: Dec. 15, 2011

(65) Prior Publication Data
US 2013/0038633 A1    Feb. 14, 2013

Related U.S. Application Data

(60) Provisional application No. 61/353,377, filed on Jun. 10, 2010.

(51) Int. Cl.
*G09G 5/00* (2006.01)
*G06T 19/00* (2011.01)
(Continued)

(52) U.S. Cl.
CPC ............ *G06T 19/006* (2013.01); *B01D 65/104* (2013.01); *B01J 19/0033* (2013.01); *B01L 99/00* (2013.01); *C12M 41/48* (2013.01); *G01N 15/0826* (2013.01); *G06T 7/004* (2013.01)
USPC ......................................................... 345/633

(58) Field of Classification Search
None
See application file for complete search history.

(56) References Cited

U.S. PATENT DOCUMENTS 7,787,992 B2 *   8/2010   Pretlove et al. ................ 700/259
8,615,374 B1 *  12/2013   Discenzo ....................... 702/127
(Continued)

FOREIGN PATENT DOCUMENTS

DE    39 17 856       12/1989
DE    102 39 831       3/2004
(Continued)

OTHER PUBLICATIONS

International Search Report of Oct. 17, 2011.
(Continued)

*Primary Examiner* — Ryan R Yang
(74) *Attorney, Agent, or Firm* — Gerald E. Hespos; Michael J. Porco; Matthew T. Hespos

(57) ABSTRACT

An assembling method for assembling a measurement or production set-up includes providing an augmented reality system with a processing device, an output device and a sensing device. The sensing device captures sensing data belonging to a working space. The method then includes providing first and second set-up components having first and second markers at the working space where the second set-up component is connectable to the first set-up component. The method captures the first and second markers by the sensing device and identifies the first and second marker. The processing device retrieves respective digital information assigned to the identified first and second markers from a database and makes a decision on the compatibility of the first set-up component with the second set-up component based on the retrieved digital information. An augmented representation of at least part of the captured sensing data and the decision on the compatibility is output.

23 Claims, 16 Drawing Sheets

(51) Int. Cl.
*B01D 65/10* (2006.01)
*B01J 19/00* (2006.01)
*B01L 99/00* (2010.01)
*C12M 1/36* (2006.01)
*G01N 15/08* (2006.01)
*G06T 7/00* (2006.01)

(56) References Cited

U.S. PATENT DOCUMENTS

2002/0044104 A1 4/2002 Friedrich et al.
2003/0144756 A1 7/2003 Koehler et al.
2004/0238420 A1 12/2004 Oldendorf et al.
2005/0102050 A1 5/2005 Richey
2006/0241792 A1* 10/2006 Pretlove et al. ............... 700/83

FOREIGN PATENT DOCUMENTS

WO 01/63468 8/2001
WO 03/045529 6/2003

OTHER PUBLICATIONS

Written Opinion of the International Searching Authority.

* cited by examiner

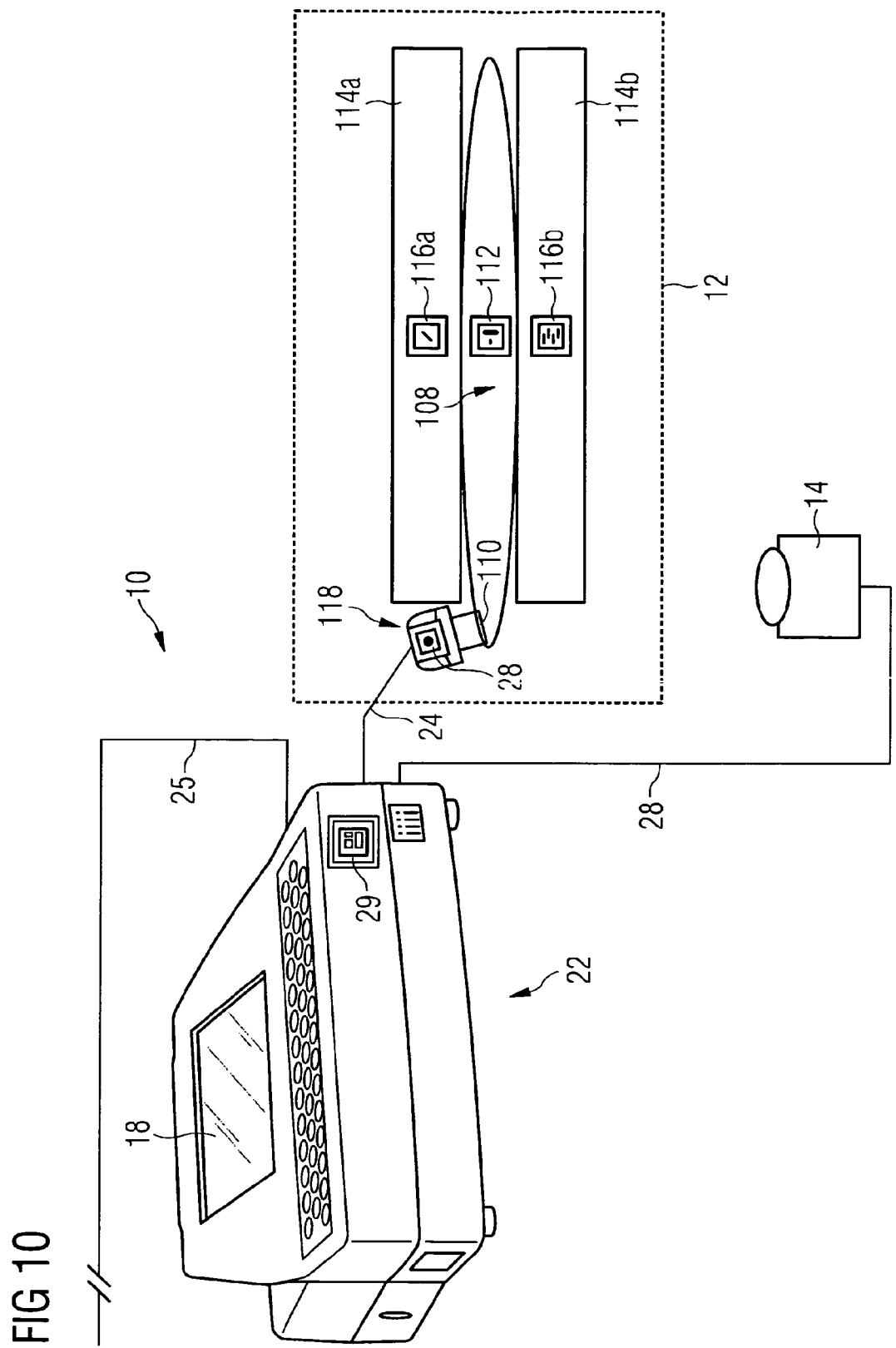

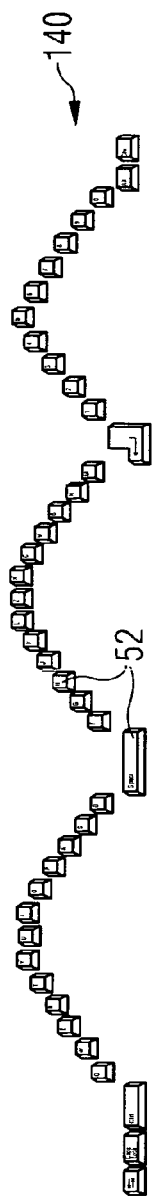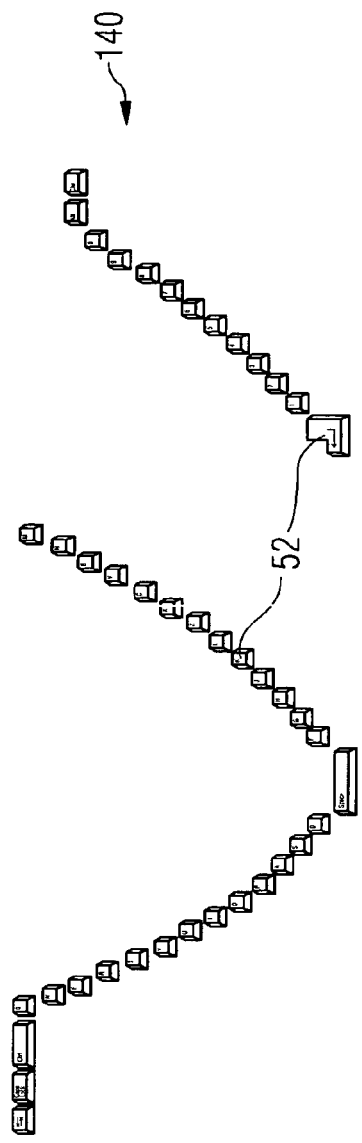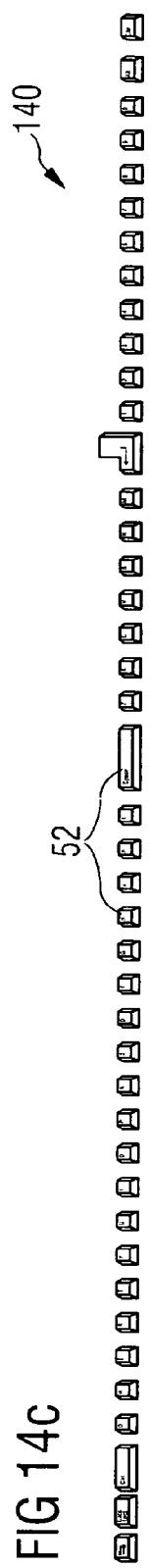
FIG 14a
FIG 14b
FIG 14c

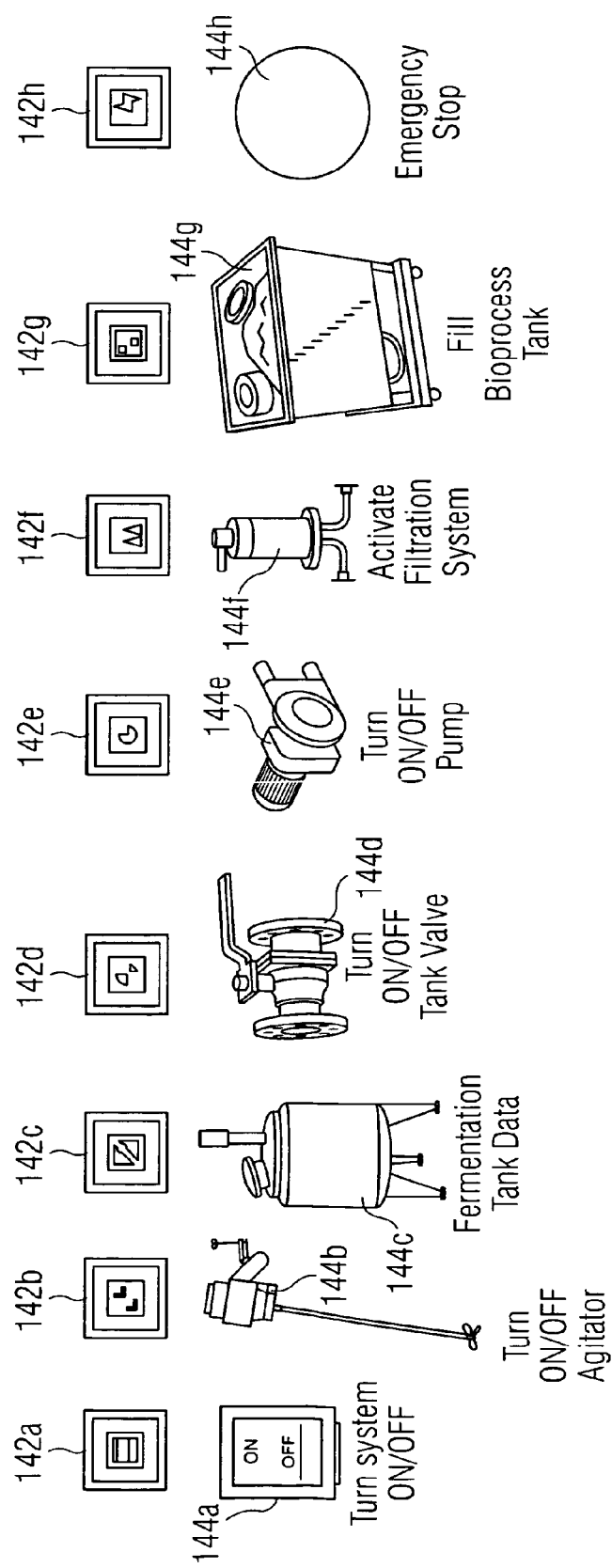

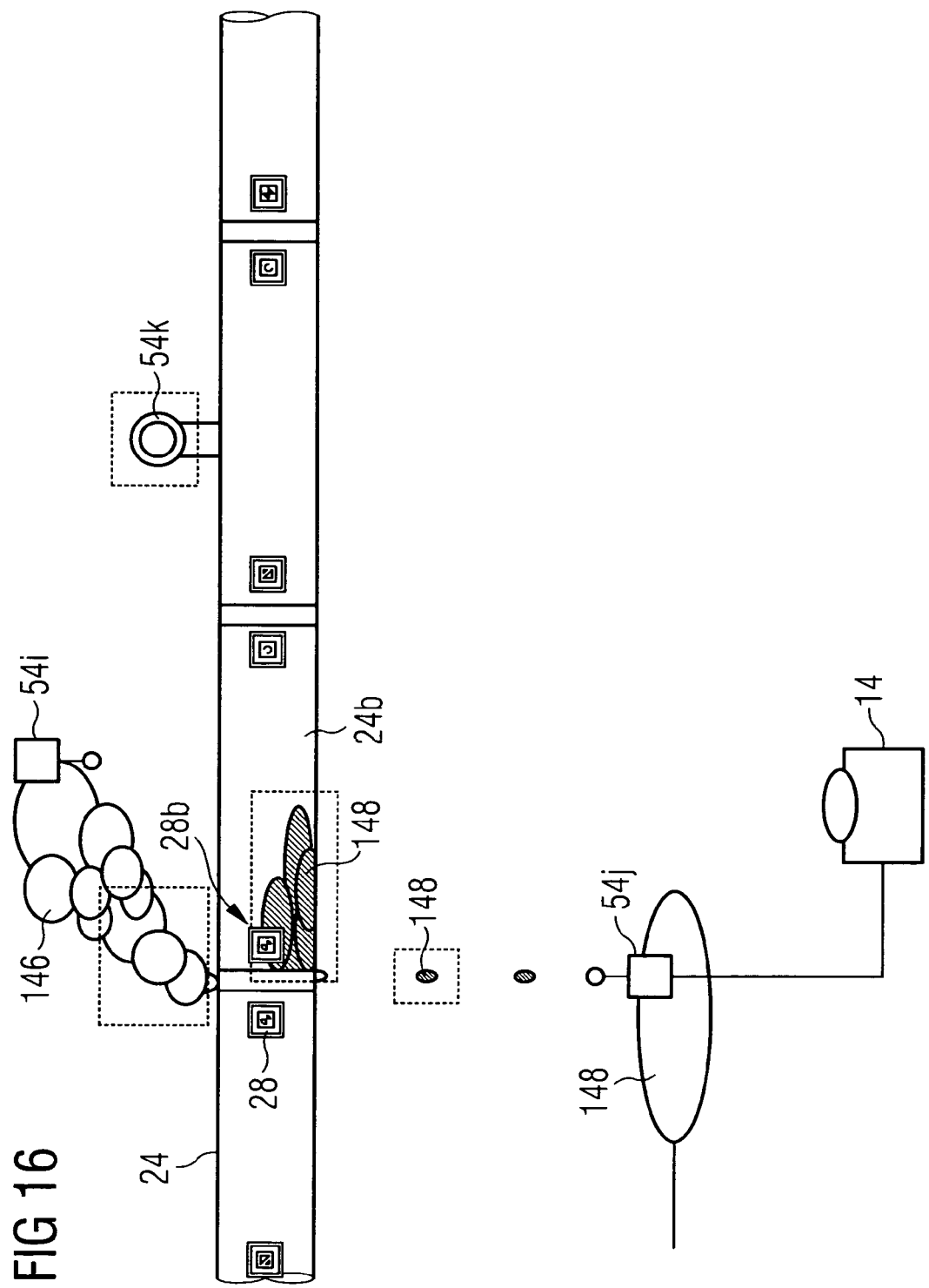

ASSEMBLING METHOD, OPERATING METHOD, AUGMENTED REALITY SYSTEM AND COMPUTER PROGRAM PRODUCT

BACKGROUND OF THE INVENTION

1. Field of the Invention

The present invention relates to improvements for the assembling of a measurement or production set-up.

2. Description of the Related Art

It is known in the art to assemble measurement or production set-ups manually from a plurality of components. For this purpose, the respective technical data of the components are typically obtained by technical data sheets. Before the assembly of the components an operator has to study all technical data sheets and select feasible components in order to assemble the set-up according to predetermined specifications.

Thus, an object of the present invention is to propose a method, a computer program product and an augmented reality system that permit an efficient assembly of a measurement or production setup.

SUMMARY OF THE INVENTION

One aspect of the invention provides an assembling method for assembling a measurement or production set-up comprising the steps:
  providing an augmented reality system with a processing device, an output device and at least one sensing device, whereby the at least one sensing device is capable of capturing sensing data belonging to a working space;
  providing a first set-up component having at least one first marker at the working space;
  providing a second set-up component having at least one second marker at the working space, wherein the second set-up component is connectable to the first set-up component;
  capturing the first marker and the second marker by the at least one sensing device;
  identifying the first and second marker, whereby the processing device retrieves respective digital information assigned to the identified first marker and second marker from a database and whereby the processing device makes a decision on the compatibility of the first set-up component with the second set-up component based on the retrieved digital information;
  outputting an augmented representation of at least part of the captured sensing data and the decision on the compatibility.

Set-ups for measurement or production may comprise various laboratory set-ups or industrial set-ups such as set-ups for testing the integrity and/or filter capacity and/or filterability of a filter device, set-ups for testing the leak-tightness of container and/or disposable bags, set-ups for charging, controlling and/or discharging bioreactors, and so on. The computer-aided assembling method using the augmented reality system can reduce the probability of erroneous assembly by an operator by automatically checking the compatibility of the assembled components or the components intended to be assembled.

The processing device can comprise a microcontroller, a microprocessor, and/or an integrated circuit configured to receive data from the at least one sensing device and transmit data to the output device. The processing device can be part of a computing system such as a PC.

The output device can comprise any one of a display device such as a monitor, a visual touch screen, a projector, a mobile device screen, a notebook or a table computer screen, a heads up display, a head mounted display (e.g. glasses having an incorporated display), a wearable display, a printer, or a haptic device, or a wired or wireless audio/visual/sensory device, or a combination of such devices. The display device can be configured for displaying the augmented image to an operator as a merged or new display with the first and/or second marker and/or the respective first and/or second component. The output device can comprise a haptic device for outputting the augmented image as a merged display or output for physically sensing the respective marker. The augmented image can be adjusted and/or displayed in accordance with the selective positioning of the respective marker by the user. The display of the augmenting image can be altered to show the merged display in real-time in accordance with the position and orientation of the physical marker.

The at least one sensing device can comprise any of the following: a camera device, a video camera, an RFID scanner device, a Global Positioning System device, a bar-code scanner device, a microphone, a laser reader device, a detector of electronic signals, a medical scanner, an electronic or visual input from industrial and/or laboratory and/or pharmaceutical equipment, a motion detection system, a visual detection system, an audio detection system, a sensory detection system, or any electronic input devices, or a combination of such devices, for the real-time detection of a position of the marker. The at least one sensing device can provide information to a processor device and/or an output device through a wired or wireless communication system. Any one of the at least one sensing devices can be powered by a powercord, a powered data cable (USB), a battery, and/or wireless power sources.

Any one of the at least one sensing devices can be located in an area of industrial manufacturing and/or a laboratory in the field of processing, mining, petrochemistry, energy, automotive, aerospace, construction, water purification, water treatment, pharmaceutics and bio-pharmaceutics near or within a working space, where the testing is carried out.

The at least one sensing device can be setup as a singular, as multiple, as remote, or as networked devices. A singular sensing device can be placed in a fixed or movable position, inside or outside of the working space and can connect directly to the processor device and/or the display device through wired or wireless connections. Multiple sensing devices can be placed in fixed and/or movable positions, inside and/or outside of the working space and may connect directly to the processor device and/or to the display device or to other sensing devices through wired or wireless connections. A remote sensing device can be placed away from the working space unit but within a remote working space connected by hosing, tubing and/or piping lines. Networked sensing devices can be located in fixed and/or movable positions, inside and/or outside of the working space and may be connected to other sensing devices or through connection hubs that can encompass multiple locations and multiple systems. These networked hubs can connect to a single processing device and/or to multiple processing devices and a single display device and/or to multiple display devices through wired or wireless connections.

According to the sensing device the sensing data can comprise image data captured at the working space by a camera, data read out from barcodes and/or RFID tags, audio data, video data, etc.

The first and second markers can be of a type that is embedded and/or mounted on devices, products, parts, items or consumables or combinations thereof in order to read a unique identification from the respective marker and/or localize the respective marker. The marker can also be the shape of the components itself. Any one of the first and second markers can comprise optical markers, such as bar codes, color codes, pictograph, the shape of items, alphanumeric characters, or electromagnetic markers, such as RFID tags, metal stripes, and so on. Any one of the first and second markers can also comprise of a simulated virtual marker that comprises of a virtual geospatial location and shape that are displayed on the display device. These simulated virtual markers can be linked to a physical marker, object, or location and can use a physical occluder to activate the simulated marker.

The working space may be a certain area on a working floor. The working space can be further delimited by a ceiling and/or at least one vertical wall. The vertical wall, the ceiling and/or the working floor may comprise a transparent material, which is transparent to visible light, to infrared radiation and/or ultraviolet radiation. The transparent material may be a glass, an acrylic glass, a transparent polymer, lead silicate, calcite and/or gypsum. In particular the working space may be enclosed by working floor, ceiling an at least one vertical wall, whereby the working space may be separated air-tight from the outside of the working space. The working floor, the ceiling and/or the at least one vertical wall can also comprise optical intransparent material as wood, plywood, metal plate, intransparent polymer, stone, brick, etc.

Components of the set-ups may be pumps, valves, filter devices, hose connections, flasks, reactors, containers, coolers, heaters, supply terminals, control devices, sensor devices such as temperature sensors, pressure sensors, optical sensors, and so on or combinations thereof. The components are connectable to each other, which may comprise a fluid connection, an electrical connection and/or a mechanical connection.

The identifying of a respective marker comprise the recognition of a marker as such and the assignment or association of the recognized marker to a unique component and/or item or to a type of identical components and/or items. The assignment between a marker and a component or type of component can be performed according to an assignment list, which can be stored in a database. Further digital information can be assigned to the identified marker within the database.

Additional digital information can include, but is not limited to, data sheets, instructions, certifications, directions for use, validation guides, replacement part lists, assembly diagrams, comparison data from previous tests, integrity test parameters or specifications; serial, model, and lot/batch numbers; reorder information, pricing information, or any other useful information to provide to the operator and/or feed the parameters into further control devices for automatically operating the set-up.

For example, data sheets and/or testing parameters can be contained in the database, which can be a local database or a remote database. The database may be divided into a plurality of local and/or remote databases each of which can contain a different type of information. Information concerning the component can also be stored in the marker itself. For example two dimensional barcodes or RFID tags comprise an amount of information storage capacity, e.g. several hundreds or thousands of bytes, in order to store specific data about the component, at which the respective marker is mounted. Most recent data sheets and updated testing parameters for recent items or products can be provided by the manufacturer or sales representative of the respective items or products via a remote database. The remote database can be made available via an internet connection, a serial connection or a telephone line.

Depending on the information retrieved from the local and/or remote database(s) the processing unit can decide upon the compatibility of the identified components. The database(s) can comprise predefined or predefinable data fields of compatible second components for the first component and vice versa. Thus, the deciding step can comprise a checking of whether the entries in each of the data fields are mutually compatible, i.e., by retrieving or calling datasets that correspond to the entries and that are stored in the database.

The step of deciding comprises a step of automatically generating a compatibility status message or error message, if the identified components are not mutually compatible. The compatibility status message and/or error message is superposed or enriched with at least part of the captured sensing data in order to obtain an augmented representation, which can be outputted to an operator. The representation regarding the compatibility status can be located near to the respective compatible or incompatible components, thus enhancing the intelligibility of the output to the operator. Incompatible components can be faster recognized and further information such as data sheets of the respective components can be outputted for further explanation of the grounds of incompatibility. Furthermore, advice can be outputted to the operator which component to replace in order to solve the compatibility problem.

According to a particular embodiment of the present invention the first set-up component is an integrity testing device. The second set-up component can be any one of an integrity testable product such as filter membranes and containers containing filtration substrates such as cartridges, capsules, columns, cassettes, tanks, and vessels; containers, disposable containers and/or multiple linked containers such as bottles, vials, bags, tubes, packaging, sterilization packaging, blister packaging, vessels, drums, tubing, piping, disposable bags, bioreactors, disposable bioreactors, spinner flasks, filter devices; or pumps, valves, hoses, and supply terminals or combinations thereof. Listed below are examples of integrity and filterability tests, which can be performed by the method according to the invention.

Integrity testing of filter membranes: Non-destructive integrity testing of filter membranes and containers containing filtration substrates such as cartridges, capsules, columns, cassettes, tanks, and/or vessels are used to confirm the retentive properties of a filter and determine if the filter contains any quality defects that are out of specification. Automated and/or manual integrity testing units perform a variety of integrity tests for pre-wetted filter membranes and filters including, but not limited to, Bubble Point, Diffusion, Bubble Point and Diffusion (combination test), Pressure Drop Test, Water Intrusion Test (WIT), Water Flow Test (WFT), Multipoint Diffusion Test, and Volume measurement tests.

Filterability testing of filters: An automated and/or manual integrity testing device can be used as a platform and/or pressure source for conducting filterability testing. Filterability testing comprises multiple trials to determine the optimal filter to use in the filtration of a particular solution, media, chemical and/or gas. Filterability testing is used to determine the optimal filter properties such as filtration area, pore size, filter geometry or the combinations of filters and pre-filters to use for a solution, media, chemical and/or gas as well as the optimal conditions for filtering including temperature, pH, pressure, and flow rate. Trials are usually run initially at the small scale and then scaled up to a process level either by larger scale filterability testing or through scale-up calculations.

Filterability challenge testing of filters: Filterability challenge testing is a destructive integrity test that is used to validate a filter's retentive performance using a challenge solution and/or aerosol containing a standard of organisms including but not limited to bacterial standard (Brevundimonas diminuta ATCC 19146 or equivalent), a mycoplasma standard (Acholeplasma laidlawii or equivalent), a viral standard (bacteriaphage PP7 or equivalent), and/or some other challenge organism. The destructive filterability challenge testing is used to establish parameters that can be correlated to nondestructive physical integrity testing results using an automated and/or manual integrity testing unit.

Integrity testing of containers: Integrity testing of containers comprises non-destructive and destructive testing to determine if there are any quality defects, gaps, holes, tears, or permeation through the container material that is outside of the specifications of the container parameters. Common containers that are integrity tested include bottles, vials, bags, tubes, packaging, sterilization packaging, blister packaging, vessels, drums, tubing, piping, and other containers that are enclosed structures or combinations thereof. Integrity testing of containers utilizes pressure hold tests, vacuum hold tests, the bubble test method, other positive or negative pressure tests, dynamic flow tests, liquid immersion tests, dye indicator tests, thermal conductivity tests, acoustic tests, or trace material detection tests (including helium leak detection, helium tracer mass spectrometry, hand probe mass spectrometry, carbon dioxide leak detection, and argon trace gas electron capture). All of these tests are used to determine if the container is properly sealed, can maintain its barrier at a specified pressure, and is able to pass the integrity testing within specifications.

Integrity testing of bags: Integrity testing of bags and bag systems (which include 2 dimensional and 3 dimensional bags) are used to determine if there are any quality defects, gaps, holes, tears, or permeation through the bag material that is outside of the specifications of the container. Integrity testing of bags and bag systems utilizes pressure hold tests, inflation testing, vacuum hold tests, positive or negative pressure tests, liquid immersion tests, dye indicator tests, or trace material detection tests. All of these tests are used to determine if the bags or bag systems are properly sealed with particular attention that the bags are able to maintain its barrier at a specified pressure without deformity; that the bag welds, seams, and seals are intact; that bag ports, valves, and integrated equipment such as mixers, probes, and filters are properly sealed; that the permeability of the bag material does not exceed specification; and that the bags are able to pass the integrity testing within specified parameters. Bag and bag systems can be used as primary or secondary packaging of materials and can be used as a barrier before and after sterilization.

Integrity testing of closed systems: Integrity testing of a closed system includes performing testing on multiple linked containers simultaneously. Integrity testing of these closed systems comprises nondestructive and destructive testing to determine if there are any quality defects, gaps, holes, tears, cracks, misaligned connections, or permeation throughout the closed system that is outside of the specifications of the system parameters. Closed systems include any linked system of integrity testable products including but are not limited to isolators, barrier systems, rooms, aseptic facilities, aseptic connections, sterilization systems (clean-in-place, steam-in-place, autoclaves, gamma irradiation, ethylene oxide sterilization, vaporized hydrogen peroxide, or clean steam systems), commercial manufacturing and packaging lines, as well as any combination of linked tanks, vessels, containers, filters, bottles, tubing, piping, and bag systems. Integrity testing of closed systems utilizes pressure hold tests, vacuum hold tests, other positive or negative pressure tests, liquid immersion tests, dye indicator tests, or trace material detection tests. All of these tests are used to determine if the closed system is properly sealed, can maintain its barrier at a specified pressure, and is able to pass the integrity testing within specifications.

Integrity testing of seals: Integrity testing of seals comprises non-destructive and destructive testing to determine if there are any quality defects, gaps, holes, tears, or permeation through the seal that is outside of the specifications of the seal parameters. Seals that are commonly integrity tested include caps, stoppers, plugs, syringes, safety packaging, connections, gaskets, O-Rings, ports, bonding, sealants, or adhesives that seal an integrity testable product. Integrity testing of seals utilizes visual inspection, internal pressure testing, pressure hold tests, vacuum hold tests, the bubble test method, other positive or negative pressure tests, dynamic flow tests, liquid immersion tests, dye indicator tests, thermal conductivity tests, corona beam tests, acoustic tests, or trace material detection tests (including helium leak detection, helium tracer mass spectrometry, hand probe mass spectrometry, carbon dioxide leak detection, and argon trace gas electron capture). All of these tests are used to determine if the seal is properly seated, can maintain its barrier at a specified pressure, and is able to pass the integrity testing within specifications.

The first set-up component can be a container controlling unit. The container controlling unit can comprise an incubated container controlling device, which can be integrated to the processing device or separate therefrom. The container controlling unit can further comprise the respective associated equipment to manually or automatically operate the measurement or production set-up, wherein the associated equipment can comprise valves, pumps, containers, filters, hoses, and so on, which can be computer controllable.

The second set-up component can be any one of an integrity testable product, a container, a disposable container, a disposable bag, a bioreactor, a disposable bioreactor, a spinner flask, a filter device, a pump, a valve, a hose, and a supply terminal.

The assembling method can comprise the step of generating an enabling instruction in case the first set-up component is compatible to the second set-up component.

The assembling method can comprise the steps:
  determining the spatial distance between the first marker and the second marker based on the sensing data captured by the at least on sensing device, wherein the processing device makes a decision on a correct connection of the first set-up component with the second set-up component based on the determined spatial distance;
  output an augmented representation comprising a representation of the decision on the correct connection.

The assembling method can comprise the steps:
  determining the location of a component to be assembled by an operator;
  display the location of the component to the operator.

One aspect of the invention provides an operating method for operating a measurement or production set-up comprising the steps:
  providing an augmented reality system with a processing device, an output device and at least one sensing device, whereby the at least one sensing device is capable of capturing sensing data belonging to a working space;
  providing a first set-up component with a first marker at the working space;

capturing the first marker by the at least one sensing device;
identifying the first marker, whereby the processing device retrieves digital information assigned to the identified first marker from a database and whereby the processing device provides a set of instructions for performing the measurement or production using the first set-up component based on the retrieved digital information;
output an augmented representation of at least part of the captured sensing data and at least part of the retrieved digital information;
perform the measurement or production operation according to the set of instructions.

The operation of the measurement or production set-up can be automatical, for example the set-up can be automatically or semi-automatically controlled by a computer or by the processing device. The respective parameters for operating can be provided by means of a database, for example a remote database. Thus, the input of the parameters to the system, i.e. to the database, can located apart from the location the set-up.

The retrieved digital information assigned to the identified first marker may contain information regarding the compatibility of the first set-up component with a second set-up component. The information regarding the second set-up component can be hardwired in the processing device or may be provided by a manual input of an operator or by a storage medium. In case of an incompatibility of the first and second set-up component, the set of instructions for performing the measurement or production can comprise the instruction to halt the operation or not to start the operation as well as an instruction to the operator to exchange the incompatible set-up component with a compatible one.

The first set-up component can be any one of an integrity testing device, a container controlling unit, a hose, a pump, a valve, a tank, a piping, an integrity testable product, a container, and an incubated container, such as a bioreactor, a disposable bioreactor, a fermentation tank, a fermentation equipment, an incubator, a medical incubator, an animal/livestock incubator, an incubated shaker, a cell/virus culture vessel, a tissue culture vessel, a disposable incubated vessel, or a disposable bag.

The first set-up component can be monitored by the at least one sensing device during the measurement or production operation, wherein the processing device generates an alert notice if the monitored data deviates from expected data beyond a predetermined variation, wherein the expected data and/or the tolerable variation is retrieved from the database. Additionally, measurement values captured by at least one associated sensor can also be monitored and a deviation of the measurement values from expected values beyond a predetermined variation can cause the processing device to generate an alert notice. The at least one associated sensor can comprise a temperature sensor, a weight sensor, a pressure sensor, a pH value sensor, a dissolved oxygen sensor, etc., which can capture the respective physical properties of any set-up component or a fluid or any other matter contained in the set-up component. {Anspruch 10} The monitored data of the at least one sensing device and/or the monitored data of the at least one associated sensor can be recorded to a database.

The operating method can comprise the steps:
providing a second set-up component connectable to the first set-up component;
capturing a second marker of the second set-up component by the at least one sensing device;
identifying the second marker, whereby the processing device retrieves digital information assigned to the identified second marker from a database and whereby the processing device makes a decision on the compatibility of the first set-up component with the second set-up component based on the retrieved digital information;
output an augmented representation of at least part of the captured sensing data and the decision on the compatibility;
perform the measurement or production in case the first set-up component is compatible with the second set-up component.

The second set-up component can be an integrity testing device or a container controlling unit and wherein the operating method comprises the step of sending an enabling instruction to the integrity testing device or to the container controlling unit in case the first set-up component is compatible to the second set-up component.

The container controlling unit can comprise an incubated container controlling device, which can be integrated to the processing device or separate therefrom. The container controlling unit can further comprise the respective associated equipment to manually or automatically operate the measurement or production set-up, wherein the associated equipment can comprise valves, pumps, containers, filters, hoses, and so on, which can be computer controllable. The integrity testing system can host the processing device of the augmented reality system or be separate from it. Sending an enabling instruction can prevent to run the production operation with incompatible set-up components.

The operating method can comprise the steps:
determining the spatial distance between the first marker and the second marker based on the sensing data captured by the at least one sensing device, wherein the processing device makes a decision on a correct connection of the first set-up component with the second set-up component based on the determined spatial distance;
output an augmented representation comprising a representation of the decision on the correct connection.

The operating method can comprise the steps:
capturing a time series of images of the working space comprising at least the first set-up component;
comparing at least two images of the time series of images;
determining a change between the at least two images;
output a message in case a change between the at least two images occur near the first set-up component.

The comparison is performed at least between a prior captured image and a more recent captured image. In case a leakage of a liquid occurs at the location of the set-up component, such as a connector or a supply terminal, and/or at the at least one hose and/or pipe the more recent image, which captures the leakage situation, would differ in shape from the prior image not showing a leakage situation. In particular the liquid leaking can at least partially cover one of the captured markers. The captured images can be transformed to a Fourier space by a Fourier transform in order to make the comparison of the images translation invariant. In other words a lateral translation of a connector and/or a hose and/or a pipe and the resulting shift of the connector, hose and/or pipe within a more recently captured image compared to a prior captured image would not lead to difference in the Fourier space and, thus, no change would determined between both images. However, a difference in shape caused by a leakage would cause differences in the Fourier space.

In particular the operating method can be configured to operate a measurement set-up for testing the integrity of an integrity testable product. In other words the operating method comprises to perform a testing method. Thus, a first set-up component can be an integrity testable product with at least one product marker as a first marker. A second set-up component can be a test set-up component having a product marker as second marker. Thus, one aspect of the invention provides a testing method for testing the integrity of an integrity testable product comprising the steps:

- providing an augmented reality system with a processing device, an output device and at least one sensing device, whereby the at least one sensing device is capable of capturing sensing data belonging to a working space;
- providing an integrity testable product with at least one product marker at the working space;
- providing at least one test set-up component connectable to the integrity testable product;
- capturing the product marker by the at least one sensing device;
- identifying the product marker, whereby the processing device retrieves digital information assigned to the identified product marker from a database and whereby the processing device makes a decision on the compatibility of the integrity testable product with the test setup component based on the retrieved digital information;
- output an augmented representation of at least part of the captured sensing data and the decision on the compatibility;
- perform the integrity test in case the integrity testable product is compatible with the test setup component.

The use of the augmented reality system with integrity testing units for the purposes of integrity testing and/or filterability testing is intended to make the process and use of integrity testers easier and more accessible through the access of relevant information and/or real-time training. Integrity testing units, integrity testable products, their connections and associated parts containing physical markers can be captured by at least one sensing device, processed by a processing device operated by an augmented reality software capable of recognizing the captured physical marker. The augmented reality software retrieves information from a local database and/or from a networked database and can superimpose at least a part of the retrieved data, such as compatibility information, onto or near the marker on a display device as an augmented display.

The augmented reality system can detect the physical relationship between multiple physical and/or simulated virtual markers to provide a user with information about the equipment, materials, samples, or items to be used with an integrity testing device, integrity testable products, their connections and associated parts; for location of parts and the verification of the correct assembly of equipment; to track the movements of those markers and/or user physical movements for step-by-step training instructions; for the evaluation of proper technique for a predetermined task; for troubleshooting integrity testing issues using a local and/or networked database or from a networked technical support system; and for receiving real-time data and control of the equipment on a visual, audio, and/or haptic display through the use of augmented reality on networked or mobile devices.

Integrity testing offers a non-destructive method for testing individual products when they are produced, prior to use, post-use, or when they are in-use or through conducting destructive testing on a representative number of samples to verify that the quality of a product is within specifications. Integrity testing comprises confirming that the seal, barrier, permeability, or retention properties of a surface, membrane, container, or closed system are within a defined specification through the use of physical, electronic, or visual testing methods. Physical methods involve using air and/or liquids or a trace material which are used to detect the differences in measured pressure or trace material to confirm if they cross a physical barrier in or around the product. Integrity tests used to determine the integrity of a sealed container, surface, membrane, or closed system include but are not limited to diffusion, bubble point, pressure drop, pressure hold/decay, forward flow, and water intrusion testing for filters and filter membranes; pressure testing, leak testing, package integrity testing and membrane integrity testing for vessels, containers, or closed systems; seal integrity testing for seals or barriers; and other associated tests used depending on the integrity testable product. Electronic methods of integrity testing comprises placing and energy source near an object such as an electric field or pulse over a membrane, compression or sound waves through a structure, or ultrasound on a surface to determine if the quality of the integrity testable product, its construction, or its ability to perform a task is within specification. Visual methods for integrity testing include inspection of intrusion by using a dye and/or trace material into a container, smoke testing of a sealed container or membrane, or the use of infrared thermal imaging to determine areas of heat exchange due to gaps in the structure of the integrity testable product.

The at least one test set-up component can be any one or a combination of an integrity testable product, a container, a disposable container, a disposable bag, a bioreactor, a disposable bioreactor, a spinner flask, a filter device, a pump, a valve, a hose, a T-connector and a supply terminal. The at least one test set-up component is connectable to the integrity testable product in order to establish a fluid connection, a mechanical connection and/or an electrical connection between both.

One of the at least one test setup components can be an integrity testing device. The testing method can comprise the step of sending an enabling instruction to the integrity testing device in case the at least one testing setup component is compatible to the integrity testable product.

The testing method can comprise the step of identifying the component marker, wherein the processing device retrieves digital information assigned to the identified component marker from a database and wherein the processing device makes a decision on the compatibility of the integrity testable product with the test setup component based on the retrieved digital information.

The testing method can comprise the steps:
- determining the spatial distance between the product marker and the component marker based on the sensing data captured by the at least one sensing device, wherein the processing device makes a decision on a correct connection of the integrity testable product with the test setup component based on the determined spatial distance;
- output an augmented representation comprising a representation of the decision on the correct connection.

The testing method can comprise the steps:
- capturing a time series of images of the working space comprising at least one fluid connection and/or at least one hose;
- comparing at least two images of the time series of images;
- determining a change between the at least two images;
- output a message in case a change between the at least two images occur near the comprising at least one fluid connection and/or at least one hose.

In particular the operating method can be configured to operate a production set-up having a container, such as a for producing a microbiological or pharmaceutical product in an incubated container using microorganisms. Thus, a first set-up component can be a container, e.g. an incubated container, with at least one container marker as a first marker. Thus, one aspect of the invention provides an operating method for operating a measurement or production set-up comprising the steps:

providing an augmented reality system with a processing device, an output device and at least one sensing device, whereby the at least one sensing device is capable of capturing sensing data belonging to a working space;

providing a container with at least one container marker at the working space;

capturing the container marker by the at least one sensing device;

identifying the container marker, whereby the processing device retrieves digital information assigned to the identified product marker from a database and whereby the processing device provides a set of instructions for performing the measurement or production using the container based on the retrieved digital information;

output an augmented representation of at least part of the captured sensing data and at least part of the retrieved digital information;

perform the measurement or production according to the set of instructions.

The container can be monitored by the at least one sensing device during the measurement or production operation, wherein the processing device generates an alert notice if the monitored data deviates from expected data beyond a predetermined variation, wherein the expected data and/or the tolerable variation is retrieved from the database. As described previously, measurement values captured by at least one associated sensor can additionally be monitored and a deviation of the measurement values from expected values beyond a predetermined variation can also cause the processing device to generate an alert notice.

A second set-up component can be a production set-up component having a component marker as second marker. The operating method can comprise the steps:

providing at least one production set-up component connectable to the container;

capturing a component marker of the production set-up component by the at least one sensing device;

identifying the component marker, whereby the processing device retrieves digital information assigned to the identified component marker from a database and whereby the processing device makes a decision on the compatibility of the container with the production set-up component based on the retrieved digital information;

output an augmented representation of at least part of the captured sensing data and the decision on the compatibility;

perform the measurement or production in case container is compatible with the production set-up component.

As previously described, the at least one production set-up component can be a container controlling unit. The container controlling unit can receive an enabling instruction in order to initiate the production only in case that the at least one production set-up component is compatible to the container. This feature can prevent to run the production operation with incompatible components.

The invention further provides a computer program for a computer-aided assembly of a measurement of production set-up and a computer program product for automatically testing the integrity of an integrity testable product or for automatically operating a measurement or production set-up, wherein the computer program comprises coding segments that when loaded and executed on a suitable system can execute a testing method and/or an operating method in accordance with the invention or an embodiment thereof. The computer programs can be loaded individually or commonly, directly or indirectly into the internal memory of a computer.

One aspect of the invention provides an augmented reality system for operating a measurement or production set-up, the augmented reality system comprising:

at least one sensing device capable of capturing sensing data belonging to a working space;

a processing device, which is in communicatively connected to the at least one sensing device, and which is capable of detect the presence of a first marker of a first set-up component in the sensing data captured by the at least one sensing device, identifying the first marker, retrieve a digital information assigned to the identified first marker, and making a decision on the compatibility of the first set-up component with a second set-up component based on the retrieved digital information and/or operating the measurement or production set-up according to a set of instructions contained in the retrieved digital information;

an output device for outputting an augmented representation of at least part of the captured sensing data as well as the decision on the compatibility and/or at least a part of the retrieved digital information.

The augmented reality system can be configured to automatically control or operate the measurement or production set-up, for example the set-up can be controlled by a computer or by the processing device. The respective control parameters for operating can be provided by means of a database, for example a remote database. Thus, the input of the parameters to the system, i.e. to the database, can be located apart from the location the set-up. The additional information regarding the compatibility of the first set-up component can be stored in a remote database, for example a database hosted by the manufacturer of the first set-up component. Thus, the compatibility information can be updated frequently.

The at least one sensing device can be any one of a camera, a still camera, a video camera, an RFID reader, a Global Positioning System device, a bar-code scanner, a microphone, a laser reader, a detector of electronic signals, a medical scanner, an electronic or visual input from industrial/laboratory/pharmaceutical equipment, a visual detection system, an audio detection system, a sensory detection system, inductive or capacitive sensor, a magnetic field sensor or any electronic input devices, or a combination of such devices.

The output device can be any one of a monitor, a touch screen, a mobile device screen, a notebook or tablet computer screen, a projector, a heads up display, a head mounted display, a wearable display, a haptic device, a braille reader, a loudspeaker, a wired or wireless audio/visual/sensory device, or a combination of such devices.

The at least one sensing device can be a camera, for example a digital video camera capable for continuously tracking the spatial position of a marker within its field of view. The camera can be a mobile camera, which can be wired or wireless connected to the processing device. With a mobile camera the operator is able to bring the camera into arbitrary positions in order to be able to bring components or marker into the field of view of the mobile camera, which may be occluded otherwise. For example a plurality of components may be arranged close together, so that a fixed camera is not able to capture the respective markers of the components. By using the mobile camera, these markers can be captured and recognized.

The system can comprise an integrity testing device or a container controlling unit, which can automatically control the respective measurement or production set-up.

The at least one sensing device and the output device can be part of a mobile device. In other words the mobile device comprise the output device, such as a display or a touch screen, and at least one sensing device, wherein further sensing devices not part of the mobile device may be connected to the mobile device, in particular to the output device, via a wired or wireless connection. Furthermore, the processing device can be part of the mobile device. In other words the augmented reality system can be designed as a mobile device, such as a smartphone or a mobile computer.

The mobile device can be connected to an integrity testing device or a container controlling unit of the system via a wireless connection. Thus, the operation of the measurement or production set-up can be controlled by means of the mobile device.

The output device can be a projector projecting the augmented representation onto the working space or onto a set-up component, whereby the augmented representation is adjusted and displayed in accordance with the spatial distribution of the component. The spatial distribution of the component as well as the spatial distribution of the floor, ceiling or a wall of the working space can be determined by a recognition of markers attached to or near to the desired projection surface. This surface can be inclined with respect to a projection beam of the projector or the surface can be irregularly shaped. The augmented representation can be adjusted respectively, for examples by a keystone correction, by the output device or by the processing device.

Accordingly, the invention provides a mobile device running a computer program product in order to carry out a computer-aided assembling method according to the invention and additionally or alternatively running a computer program in order to carry out an automatically operating method for controlling a measurement or production set-up.

BRIEF DESCRIPTION OF THE DRAWINGS

FIG. 10 shows an augmented reality system for testing the integrity or leak tightness of integrity testable products.

FIGS. 14a-c preferred layouts of a virtual keyboard.

FIG. 15 different types of components represented by different assigned pictograph markers.

FIG. 16 is a schematic illustration of an augmented reality system configured to check for and monitor a leak.

DETAILED DESCRIPTION OF THE PREFERRED EMBODIMENTS

Figure 1:
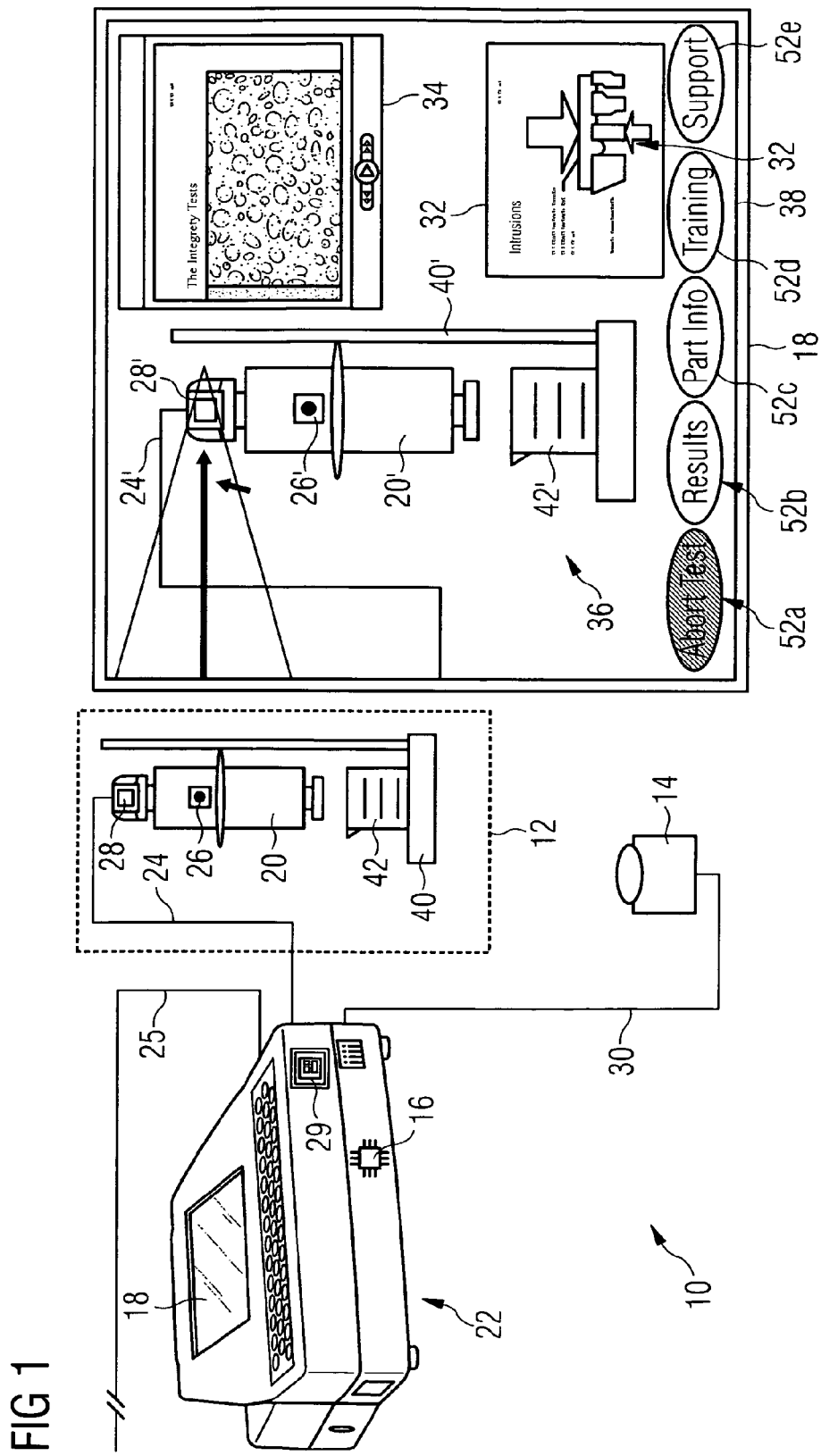
FIG. 1 illustrates a preferred embodiment of an augmented reality system.
Figure 2:
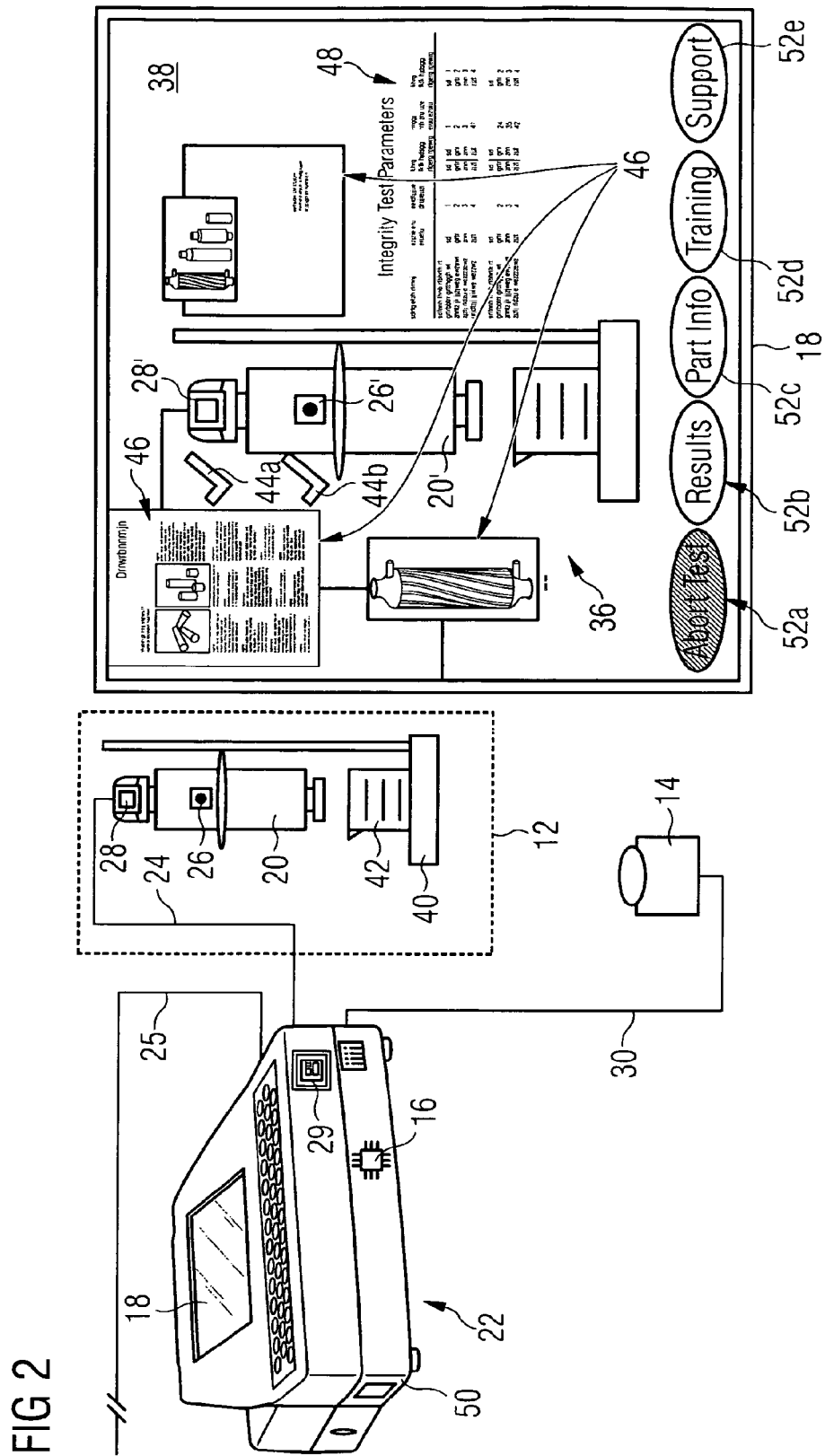
FIG. 2 shows the system of FIG. 1 at a later stage.

FIGS. 1 and 2 show an augmented reality system 10 for testing the integrity and/or filter capacity and/or filterability of a filter device 20 located in a working space 12. The augmented reality system comprises at least one sensing device 14, a processing device 16, an augmented reality software, and at least one display system 18.

The at least one sensing device 14 is configured to detect at least one type of marker that is embedded and/or mounted on devices, products, parts, items or consumables in order to read a unique identification from the marker and/or localize the marker. As shown in FIGS. 1 and 2 the at least one sensing device 14 may comprise a camera device 14, which is adapted to capture images of a predetermined working space 12 and to provide the captured image data to the processing device 16. As shown in FIGS. 1 and 2, a testing setup including the filter device 20 can be located within the working space 12 and the testing procedure may using an integrity testing device 22 for automatically and/or manually performing an integrity test, a filter capacity test and/or a filterability test. The integrity testing device 22 can be located at least partly within the working space 12 or outside the working space 12. A fluid connection can be established between the integrity testing device 22 and the filter device 20 by a connection hose 24. The integrity testing device 22 can be configured to provide a fluid, i.e. a gas or a liquid, in order to apply a predetermined pressure via the connection hose 24 to the filtering device 20. Depending on the fluid permeability of the filter device the applied pressure can drop within a certain period of time or a certain volume of fluid can pass the filter device. In order to provide the fluid the integrity testing device 22 can be connected to a fluid source, e.g. a compressed air source, via a fluid supply hose 25.

The camera device 14 is configured to capture optical markers, e.g. bar codes, color codes, pictograph, the shape of items, alphanumeric characters etc., which may be located on the items located in the working space. As an example a filter device marker 26 in form of a pictograph is attached to the filter device 20 and a connection hose marker 28 is attached to the connection hose 24. Further an integrity test device marker 29 can be attached to the integrity test device 22.

The working space 12 may be delimited by a working floor, a ceiling and/or at least one vertical wall. The vertical wall, the ceiling and/or the working floor may comprise a transparent material, which is transparent to visible light, to infrared radiation and/or ultraviolet radiation. The transparent material may be a glass, an acrylic glass, a transparent polymer, lead silicate, calcite and/or gypsum. In particular the working space may be enclosed by working floor, ceiling an at least one vertical wall, whereby the working space may be separated air-tight from the outside of the working space 12.

The at least one camera device 14 can be positioned in the interior and/or exterior of the working space 12. In case one of the at least one camera device 14 is positioned inside the working space 12, the respective camera device 14 may be encapsulated fluidproof by a camera casing in order to avoid a contamination of the camera device 14 with chemicals and/or microorganisms from within the working space 12. In case one of the at least one camera device 14 is positioned outside the working space 12, the respective camera device 14 may be capturing the images of the working space 12 through a transparent vertical wall, ceiling or working floor. In order to enable a determination of positions of various items relative to predetermined locations of the working space 12 the working floor, the ceiling and/or the at least one vertical wall may be provided with at least one fixed marker.

The camera device 14 may be a video camera or a still camera, whereby the camera device 14 may be positioned at a fixed position relative to the working space 12 or may be movable with respect to the working space 12, thus capturing images of the working space 12 from different angles of view. In case of a mobile camera device 14, the processing device 16 may control a camera positioning device, which is configured to transfer the camera device 14 from one angle of view to another angle of view.

The camera device 14 may be sensitive to visible light, infrared radiation and/or ultraviolet radiation of at least one wavelength. The camera device 14 may repeatedly capture images of the working space, whereby the image capturing frequency may be variable or constant, e.g. larger than approximately 1 Hz, preferably approximately 25 Hz. The image data captured by the camera device 14 may be transmitted to the processing device 16 via a cable connection 30 or via electromagnetic waves. The processing device 16 is configured to process the image data captured from the at least one camera device 14 in order to extract the image of any marker, e.g. the filter device marker 26 and the connection hose marker 28, contained in the captured image data. The extracted marker image(s) may be matched with a dataset from a local or remote database in order to identify the marker and retrieve additional information belonging to the identified marker from the database or from other data sources, which location is stored in the database. Based on the retrieved additional information and the captured image data the processing device 16 can compute status information of the testing setup.

With reference to FIG. 1 a representation of the status information 32, a representation of the retrieved additional information 34 and/or at least part of the captured image data 36 can be presented to an operator on the display device 18. The display device 18 can comprise a monitor, e.g. a liquid crystal display (LCD), a cathode ray tube (CRT), a touch screen monitor and/or a projector (beamer). The display device 18 can be fixedly located, e.g. at the working space, at the processing device 16, at the integrity testing device 22 or at a distant location like a control center. Further, the display device 18 can a mobile display device, e.g. the display of a notebook computer, a tablet computer, a cell phone, a wearable display or a head mounted or heads up display.

In order to enhance the readability of the information to the operator, the processing device 16 can analyze the image data obtained from the camera device 14, identify any marker contained in the image data, link additional information retrieved from a database correlated to identified markers and superimpose the representation of the additional information 34 with a part of the image data 36 in order to generate an augmented display image 38. In the example shown in FIG. 1 the image data 36 comprises an image 20' of the filter device 20, an image 24' of the connection hose 24, an image 26' of the filter device marker 26, an image 28' of the connection hose marker 28, an image 40' of a stand 40 holding the filter device 20 and an image 42' of a beaker 42. The image data 36 and the representation of the additional information 34 can be displayed in real-time, whereby the identified markers 26', 28' can be used for positioning the representation of the additional information 34 within the augmented display image 38. The representation of the additional information 34 can comprise texts and/or graphical elements, whereby the representation of the additional information 34 and the image 20' of the correlated item, e.g. the filter device 20, comprising the respective marker can be positioned closely together within the displayed augmented image 38. Sometimes it may even be preferred that the additional information at least partly covers the correlated item shown in the augmented image 38.

The augmented reality system 10 shown in FIG. 1 can be utilized in multiple ways to assist the operator in obtaining information and/or for performing tasks related to the integrity testing device 22 and the filter device 20. The displaying of additional information about equipment, parts, consumables and/or items, e.g. the filter device 20, located in the working space 12 and/or attached to the integrity testing device 22 can be achieved by capturing the respective marker attached to or embedded in the physical item by the at least one sensing device 14, whereby a unique identification of the marker is matched with the database by the processing device 16. As an example, the filter device marker 26 attached to the filter device 20 is captured by the camera device 14, identified by the processing device 16 and additional information related to the filter device 20, which may be contained in an internal database of the processing device 16, is retrieved and a representation of the additional information 34 is displayed on the display device 18. The additional information linked to the marker can be accessed by changing the orientation or angle of the physical item, e.g. the filter device 20, or by changing the angle of view of the at least one camera device 14.

Further, the displaying of additional information can be triggered by adding another item to the working space 12, e.g. a connecting hose 24 as shown in FIG. 1, whereby the connecting hose 24 establishes a fluid connection between the filter device 20 and the integrity testing device 22. For example, in case the connection hose marker 28 attached to the connection hose 24 is detected to be within the workspace 12 as the same time as the filter device 20, identifiable by the filter device marker 26, the processing device 16 can retrieve information from the database, whether the connection hose 24 is compatible to the filter device 20. The representation of the status information 32 stating that the filter device 20 and connection hose 24 are incompatible can be displayed on the display device 18.

As a further example, displaying additional information about an item located in the working space 12 or initiating a predetermined action of the system 10 or the integrity testing device 22 can be triggered by a physical movement of the item that may change the properties of the marker or by occluding the marker of the item.

Since the augmented reality system shown in FIG. 1 can capture and detect multiple markers by means of the camera device 14 the processing unit 16 can compare the distances, the orientation, and the relationship between the detected markers based on the captured images of the working space 12. The processing unit may compare the determined distances with an local or remote database to confirm with the operator if a particular unit and/or setup is properly assembled and if corrections in the setup need to be made prior to use. This will allow the operator to have the setup of equipment located in the working space 12 checked by the augmented reality system 10. In case the setup is not assembled correctly, the processing unit may issue instructions to the display device 18 to show how to reach the correct setup prior to the use of the setup.

In particular connecting the connection hose 24 to the filter device 20 as shown in FIG. 1 can be detected by the camera device 14, since the respective markers 26, 28 of the filter device 20 and the connection hose 24 remain under a predetermined critical distance. The processing device 16 may discriminate whether the filter device 20 and the connection hose 24 are correctly connected by means of a distance measurement, the physical orientation, or a predetermined relationship between the two respective markers thereof. Instead of the distance measurement or additionally, the processing unit 16 may discriminate whether the filter device 20 and the connection hose 24 are compatible, e.g. whether both items are designed for a predetermined pressure or whether both items are designed for performing a work task under sterile conditions.

As shown in FIG. 2 one or more status indicators 44a, 44b can indicate within the augmented display image 38 whether the displayed items 20' and 24' are compatible and/or correctly connected. The respective displayed markers 26' and 28' of the displayed items 20' and 24' can serve as an origin location for a predetermined spatial location of the status indicators 44a, 44b on the display device 18. In case that the assembly of the filter device 20 and the connection hose 24 is erroneous, e.g. the filter device 20 is of a sterile type and the connection hose 24 is of a non-sterile type, which is inappropriate to be used together with the filter device 20 since the assembly cannot be used while maintaining the sterile conditions within the filter device 20, the processing unit 16 may issue instructions or data sheets 46 to the display device 18 to support the operator with appropriate information in order to use an appropriate sterile connection hose. This instructions or data sheets 46 may contain information, e.g. item numbers, model numbers etc., in order to select the correct connection hose.

In case the assembly of the testing setup is correct, information concerning the further proceedings may be displayed within the augmented display image 38. For example data sheets 46 and testing parameters 48 can be displayed on the display device 18. According to the data sheets 46 and testing parameters 48 the operator can perform the testing. The data sheets and/or testing parameters can be retrieved from a local database or from a remote database. Most recent data sheets and testing parameters for recent items or products can be provided by the manufacturer or sales representative of the respective items or products via a remote database.

With regard to the FIGS. 1 and 2, the status information and/or the retrieved additional information like the testing parameters can be used to control the integrity testing device 22. Thus, the processing device 16 can be connected via a cable or a wireless connection to the integrity testing device 22 for data exchange. Further, the processing device 16 and the integrity testing device 22 may be arranged in one housing 50. The augmented display image 38 displayed to the operator by means of the display device 18 may comprise control elements 52a to 52e for controlling the test procedure and/or for selecting predefined actions, such as retrieving information, start the testing and so on.

In case the setup is not assembled correctly, the processing unit 16 may block an activation of the integrity testing device 22 until a correct assembly is established or the operator overrides the blocking by entering an override instruction. This can be done by disabling the control element 52a for starting the testing procedure.

Figure 3:
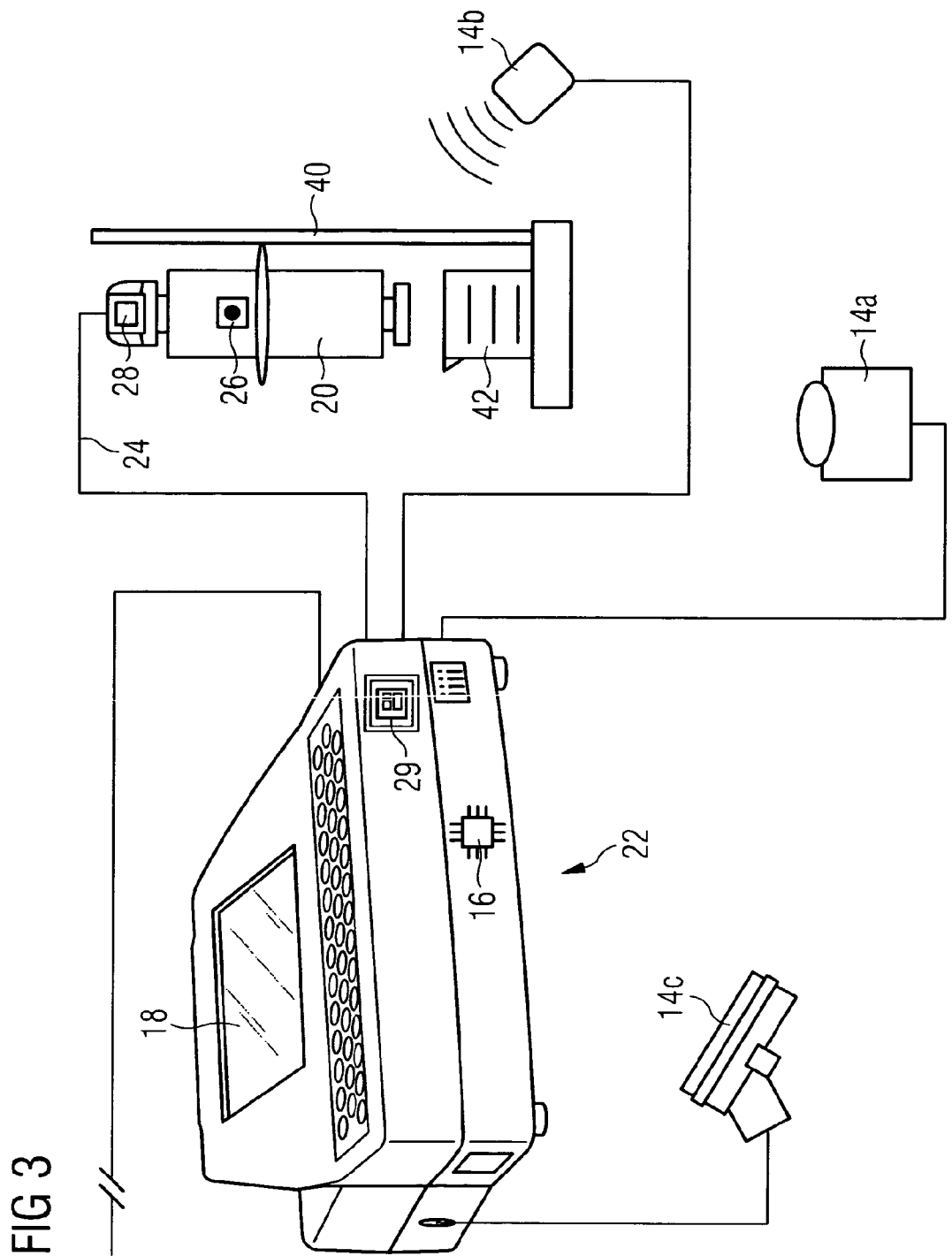
FIG. 3 shows additional features of the system of FIGS. 1 and 2.

As shown in FIG. 3 the augmented reality system 10 can comprise a plurality of sensing devices 14a, 14b, 14c. The plurality of sensing devices can comprise a plurality of the same type of sensing device, e.g. a plurality of camera devices, a plurality of RFID scanner devices or a plurality of code or bar-code scanner devices. The plurality of sensing devices can also comprise different types of sensing devices, e.g. one or more camera devices 14a, and/or one or more RFID scanner devices 14b and/or one or more bar-code scanner devices 14c. The plurality of sensing devices 14a, 14b, 14c is connected to the processing device 16, whereby the connection can be established by cables and/or by a wireless communication link.

The RFID scanner device 14b and/or the bar-code scanner device 14c can be located within the working space 12 or outside the working space 12. The scanner device 14b and/or the bar-code scanner device 14c can be encapsulated in order to prevent a contamination of the devices with chemicals and/or microorganisms. In case the working space 12 is delimited by one of a optical non-transparent working floor, ceiling and/or at least one vertical wall the RFID scanner can be located outside the working space 12 and configured to establish an electromagnetic communication connection with a RFID marker located within the working space 12. RFID markers can be attached to or embedded into an item.

For example the test setup shown in FIG. 3 can comprise a sealing ring like an O-Ring, in which a RFID readable marker (RFID tag) is embedded. The RFID tag is arranged between the connection hose 24 and the filter device 20 and, therefore, hidden to the camera device 14 shown in FIG. 3. However, the presence of the sealing ring can be detected by the RFID scanner device 14b. Based on this detection, the processing device 16 can decide whether the testing setup is completely assembled.

Figure 4:
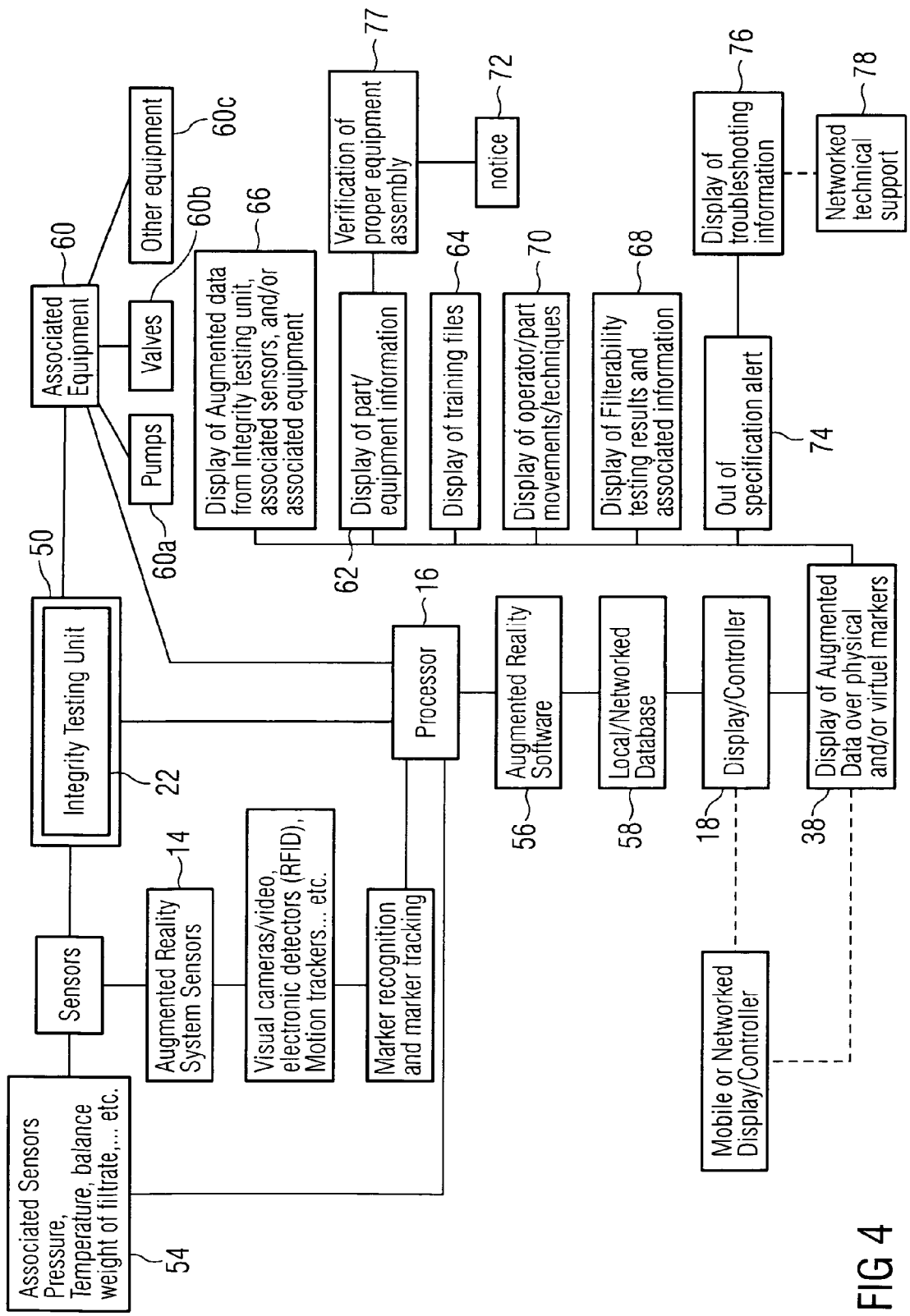
FIG. 4 illustrates the information flow during an exemplary filterability testing with the system shown in FIGS. 1 to 3.

The handling of the augmented reality system 10 as shown in FIGS. 1 to 3 by an operator is described with respect to FIG. 4, which illustrates the information flow during an exemplary filterability testing of the filter device 10. An automated and/or manual integrity testing unit 22 can be used as a platform and/or pressure source for conducting filterability testing. The filterability testing can be used to determine filter properties such as filtration area, pore size, filter geometry or the combinations of filters and pre-filters to use for a fluid, a liquid, a solution, a chemical and/or a gas as well as the conditions for filtering including temperature, pH, pressure, and flow rate.

The integrity testing device 22 is communicatively connected with associated equipment 60, e.g. with valves 60a, pumps 60b, and/or other equipment 60c which can be located together with the integrity testing device 22 within one housing or which may be located outside the housing of the integrity testing device 22. The associated equipment 22 can be required to carry out an automatic testing procedure.

The integrity testing device 22 and optionally the with associated equipment 60 can be communicatively connected with the processing device 16. The processing device 16 and optionally the integrity testing device 22 can be communicatively connected with the at least one sensing device 14 and/or at least one associated sensor 54, e.g. a temperature sensor, a weight sensor, a pressure sensor, etc., which can record the temperature, the weight, the pressure, etc. of an item or a fluid handled or contained in one of the items. The communication connection can be wired or wireless connection, like a copper cable, a glass fiber cable, or a pair of antennas.

The at least one sensing device 14 of the augmented reality system 10 shown in FIG. 4 comprises a sensing device that detects a physical marker or the occlusion of the physical marker, whereby the physical marker is attached to or embedded in an item, which can be entered into or removed from the working space 12. The processing device 16 can be integrated into the integrity testing device 22 or operate separately in conjunction with the integrity testing device 22.

An augmented reality software 56 controlling the information transfer from the integrity testing device 22, the at least one sensing device 14, the associated sensors 54 and/or the associated equipment 60 is running on the processing device 16. The augmented reality software 56 can perform the recognition and identifying of the markers contained in the data captured by the at least one sensing device 14. Further, the augmented reality software 56 can provide a local database 58 or provide an access to a remote database 58 for matching the identified markers with known markers from the database 58 and retrieve additional information (digital content) from the database 58 belonging to any one of the identified markers, respectively belonging to the item to which the respective marker is attached.

In case the operator places an item, e.g. the filter device 20, within the working space 12 the at least one sensing device 14 captures the marker of the item and the processing device 16, respectively the augmented reality software 56, identifies the item. Depending on the identified item a preselected event can occur, exemplary the retrieval of recent user instructions from the database 58. As an example of additional information a step-by-step testing instruction for the filter device 20 can be retrieved from the database 58. Also when adjustments are made to the physical marker, e.g. by relocalizing the marker or by occluding the marker, another preselected event may occur. The preselected events can be initiated by the operator by the altering the detection of the physical marker, the position or orientation of the physical marker, the relationship or distance of physical markers to other physical or simulated virtual markers, the distance between the physical marker and the sensing device, or the occlusion of a physical or virtual marker with a defined occluder. The occlusion of a physical marker with a physical object can include the occlusion by a finger or hand of the operator.

The additional information (digital content) can comprise text data, audio data, visual data, video data, training videos, step-by-step instructions, graphics, data test parameter, or any other information or program. A representation of the additional information can be superposed by the augmented reality software 56 with an image of the working space 12 or an image of any one of the items placed in the working space 12, whereby the image can be captured by one of the at least one sensing devices 14. By the superposition an augmented image 38 is generated, which can be sent to at least one display device 18 comprising a display and/or a controller for a display, whereby the display can be a remote or mobile display. The representation of the additional information can be displayed superimposed over the location of the physical and/or virtual marker or in a separate location or window on the display device 18.

The augmented reality system 10 is capable to detect and identify multiple markers embedded in and/or on equipment, devices, parts, materials, items, consumables, or fixed locations within or near the working space 12. Therefore, the augmented reality system 10 can provide the operator with additional information about the a plurality of items that comprise a respective marker. As example the augmented image may contain a respective representation of part and/or equipment information 62, like item numbers, best-before date, etc., and training information 64, like step-by-step instructions, a training video etc. Furthermore, equipment and/or devices communicatively connected to the processing device 16, such as an electronic balance or scale for filterability testing, can communicate through wires and/or wireless connections to the processor device 16 to provide real-time data, whereby a representation 66 thereof can be part of the augmented image displayed to the operator. Additionally, a representation of test results 68, e.g. the filterability testing results, may be provided and/or computed by the processing device 16 and displayed to the operator. Movements of the items captured by the at least one sensing device 14 can be detected by comparing at least two of the captured images, which were captured at different times. A representation of item movement 70, such as drawn vectors of movement or alert messages, can be displayed to the operator.

The augmented reality system is capable to resolve the spatial position of identified markers based on the data captured by the at least one sensing device 14; 14a, 14b, 14c, such as the images captured by the camera device 14; 14a. The spatial position of the marker and, thus, the correlated spatial position of the respective item includes the orientation of the marker as well as the distance and/or relationship of the marker to another marker. The spatial location of the markers within the working space 12 can be used to track and record the movements of the markers and/or physical movements of the operator to determine if proper technique of a predetermined task is being followed within some set margin of error. The tracking of markers for performing or following proper technique of a predetermined task can be used in conjunction with a step-by-step training program in which the operator is instructed, shown, and then evaluated for performance of a set task. The operator can be evaluated and graded within an operator defined system for performing or following the proper technique for a predetermined task within the margin of error by the software which tracks the movements of the markers and/or physical movements of the operator.

In case the augmented reality system 10 detects an erroneous assembly of the testing setup in the working space 12, as the above mentioned example that the filter device 20 is of a sterile type and the connection hose 24 is of a non-sterile type, the display device can display a notice 72 concerning the failed verification of proper equipment assembly.

Based on the data provided by the associated sensors 54 the processing device 16 discriminate, whether the single data values are within a specified range. In case one or more measurement values are out of the specified range, a respective alert message 74 can be displayed by means of the display device 18. Together with the alert message 74 the operator can be provided with trouble shooting information 76 based on additional information retrieved from a local and/or remote database. Additionally, the augmented reality system 10 may establish a network connection 78 in order to obtain support from a remote expert.

Figure 5:
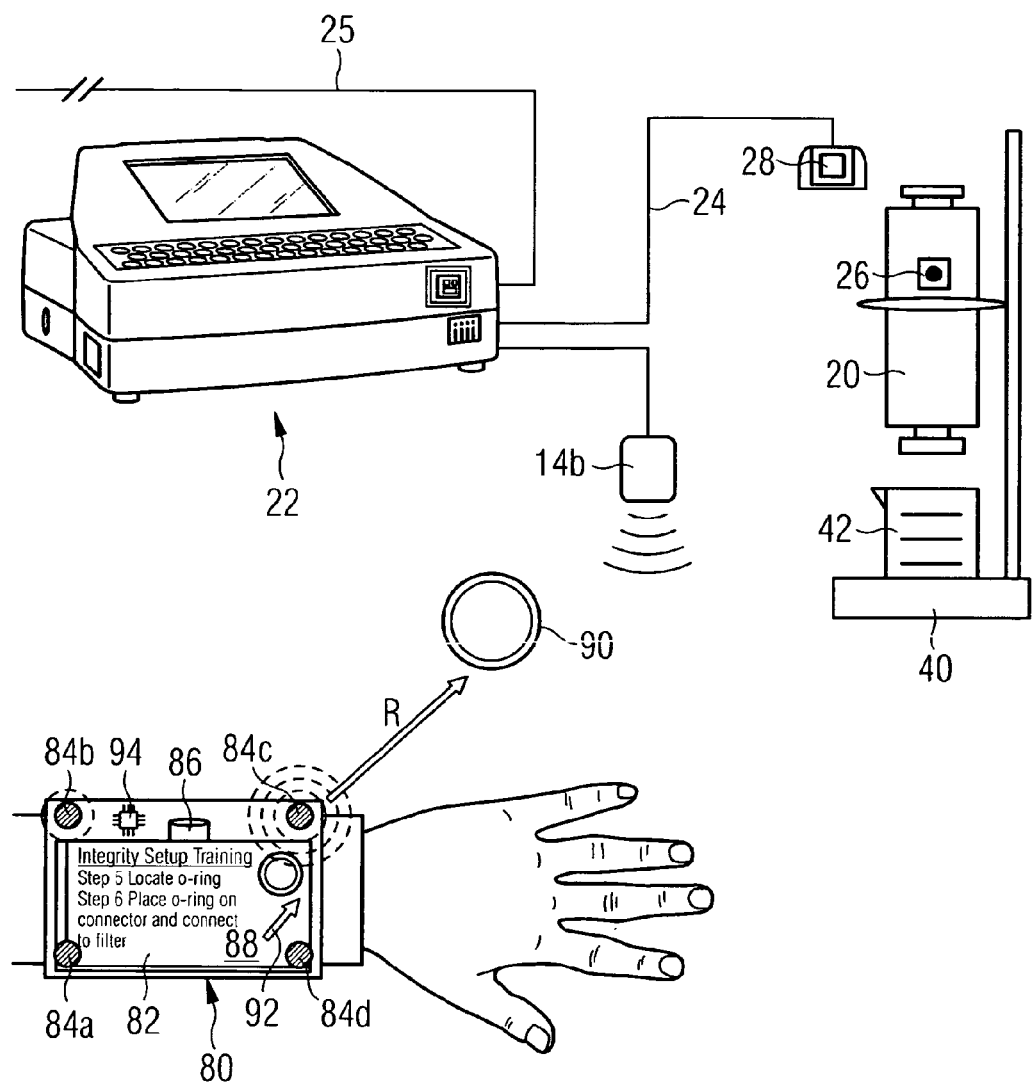
FIG. 5 shows a wireless mobile wearable device.

FIG. 5 shows a wireless mobile wearable device 80, which can communicate in real-time with the processing device 16 and/or the integrity testing device 22 as illustrated in FIGS. 1 to 4. The mobile device 80 comprise a mobile display 82 for displaying augmented data, such as a monitor and/or touch screen visual display. Further, the mobile device 80 may comprise an acoustic device (not shown) for generating audio signals. As shown in FIG. 5 the mobile device 80 can comprise at least one pressure inducing device 84a, 84b, 84c, 84d. The at least one inducing device 84a, 84b, 84c, 84d can be operated by one or more vibration motors (not shown) to provide a tactile sensation to the operator wearing the mobile device 80. The wireless mobile wearable device 80 can also include a mobile sensing device 86, such as a digital video camera 86 providing a processing device (not shown) located within the mobile device 80 with captured image data.

An augmented reality software can run on the processing device of the mobile device 80 in order to recognize markers from the data recorded by the at least one mobile sensing device 86, for example from the images captured by the digital video camera 86. Additional information linked to recognized markers and retrieved from a local and/or remote database can be displayed within an augmented reality image 88 analogous to the augmented reality image 38 described conferring to FIGS. 1 to 4. Thus, the mobile device 80 can provide the same functionality as the augmented reality system 10 described with respect to FIGS. 1 to 4.

The mobile device 80 can be worn by the operator around the wrist (like a watch or bracelet), around the arm or leg (like a blood pressure cuff), on a finger (like a finger monitor or ring), around the hand (like a glove), or attached to some other extremity or location of the body. The at least one inducing device 84a, 84b, 84c, 84d of the mobile device 80 can provide a haptic display of augmented data comprising of movements of the at least one inducing device 84a, 84b, 84c, 84d that convey a tactile sensation on the skin, whereby the tactile sensation can be controlled by the processing device of the mobile device 80 depending on information or data recorded or captured by the at least one sensing device 86 of the mobile device 80 and/or depending on additional information retrieved from the database.

As an example the at least one inducing device 84a, 84b, 84c, 84d may provide the operator with vibratory directions to the location of the next part to assemble and where to connect it. For example an O-Ring 90 may be the next part necessary for the actual assembling step. The position of the O-Ring 90 can be determined by the video camera 86 of the mobile device 80 in case the O-Ring 90 within the field of view of the video camera 86. Thus, the relative location of the O-Ring 90 can be determined based on the images captured by the video camera 86. Alternatively or additionally the O-Ring 90 can be localized by other sensing devices 14b connected to the processing device, for example by the RFID scanner 14b. The localization of the O-Ring 90 can be performed relative to an origin of the working space 12. The position and orientation of the mobile device 80 relative to the origin of the working space 12 can be determined by GPS or by detecting a marker of the working space 12, which position relative to the origin of the working space 12 is known. Based on this information the relative position of the O-Ring 90 with respect to the mobile device 80 can be computed and indicated to the operator.

The relative direction R towards the O-Ring 90 can be indicated by displaying a directional arrow 92 on the mobile display 82. Alternatively or additionally, the mobile device 80 can comprise four inducing devices 84a, 84b, 84c, 84d, this is one inducing device per one of the four directions such as front, rear, left right. The four inducing devices 84a, 84b, 84c, 84d can be used to give the operator an indication of the relative direction of the O-Ring 90. For example, the amplitude of the signal emitted by the inducing devices 84a, 84b, 84c, 84d can be dependent on the consilience of the relative direction of the O-Ring 90 with the direction of the respective inducing device 84a, 84b, 84c, 84d from the center of the mobile device 80. In other words, in case one of the inducing devices 84b directs towards the O-Ring 90, this particular inducing device 84b will emit a signal while the remaining inducing devices 84a, 84c, 84d will not emit a substantial signal.

Any one of the inducing devices 84a, 84b, 84c, 84d can include inflatable and deflatable airbags that can be inflated from an air-actuator, pump, or connected to an airbag or vessel worn by the operator containing a volume of pressurized air. A tension tightening fabric across the skin of the operator can also be used to convey increasing and/or decreasing pressure. These airbags or tension tightening fabrics can convey pressure on the skin of the operator according to predefined signals. Alternatively, vibration motors and/or an sonic source can be utilized for generating the signals emitted by the inducing devices 84a, 84b, 84c, 84d.

In an embodiment the mobile device 80 can comprise an mobile processing device 94 in addition or as alternative to the processing device 16 of the integrity testing device 22. The mobile processing device 94 can be configured to receive the sensing data captured by the at least one mobile sensing device 86, such as the images captured by the video camera 86. Thus, the mobile processing device 94 can perform the recognition and decision based on the sensing data of the at least one mobile sensing device 86 and can further generate and display an augmented image on the mobile display 82. The mobile processing device 94 may be in connection, for example in wireless connection, with further sensing devices 14b of the augmented reality system 10 and/or the integrity testing device 22 and/or the processing device 16, for example to receive sensing data from a sensing device 14b and/or to receive measurement data from the integrity testing device 22 and/or to establish a connection to a local or remote database for example via the processing device 16.

Figure 6:
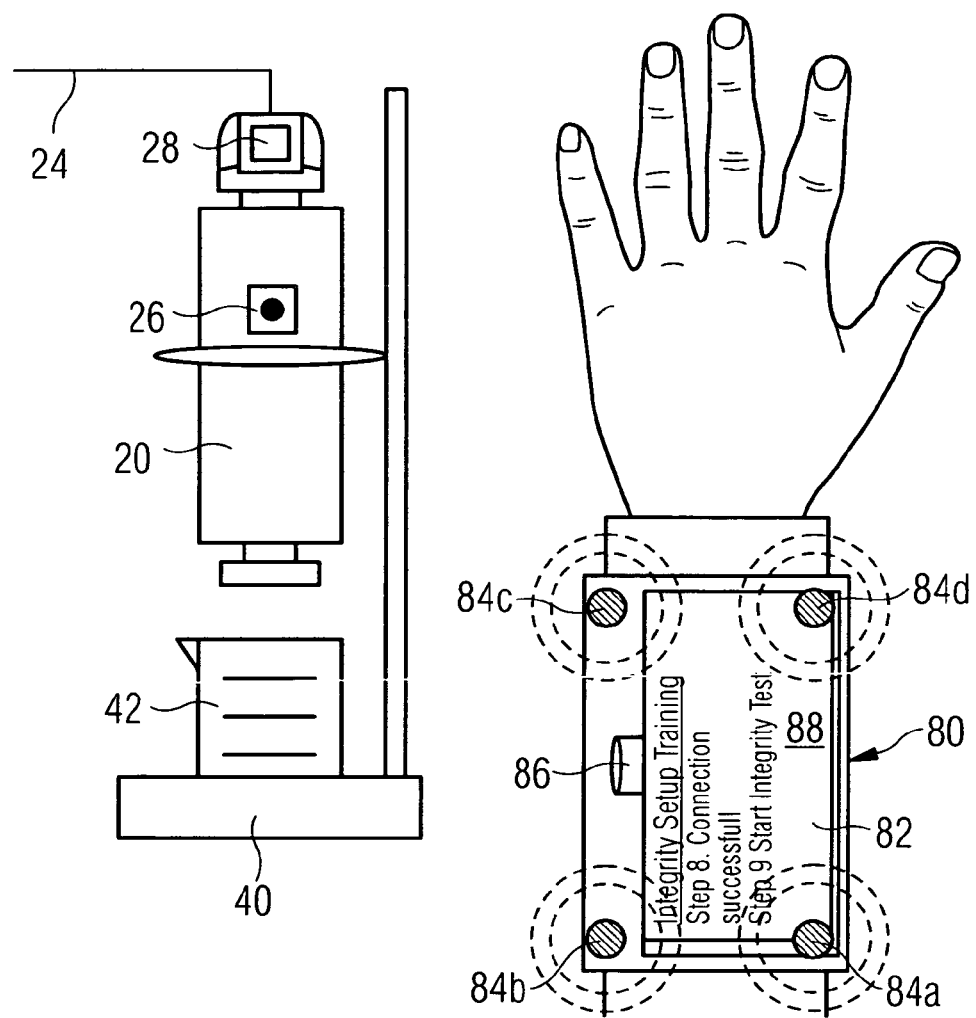
FIG. 6 shows the wireless mobile wearable device at a later time.

FIG. 6 shows the wireless mobile wearable device 80 after the successful assembly of the filter device 20 and the connection hose 24 with the intermediate O-Ring 90 (not shown). In order to inform the operator about the successful assembly all inducing devices 84a, 84b, 84c, 84d may emit a signal and/or vibration. A different signal to the operator may be given in case of an erroneous assembly.

Figure 7:
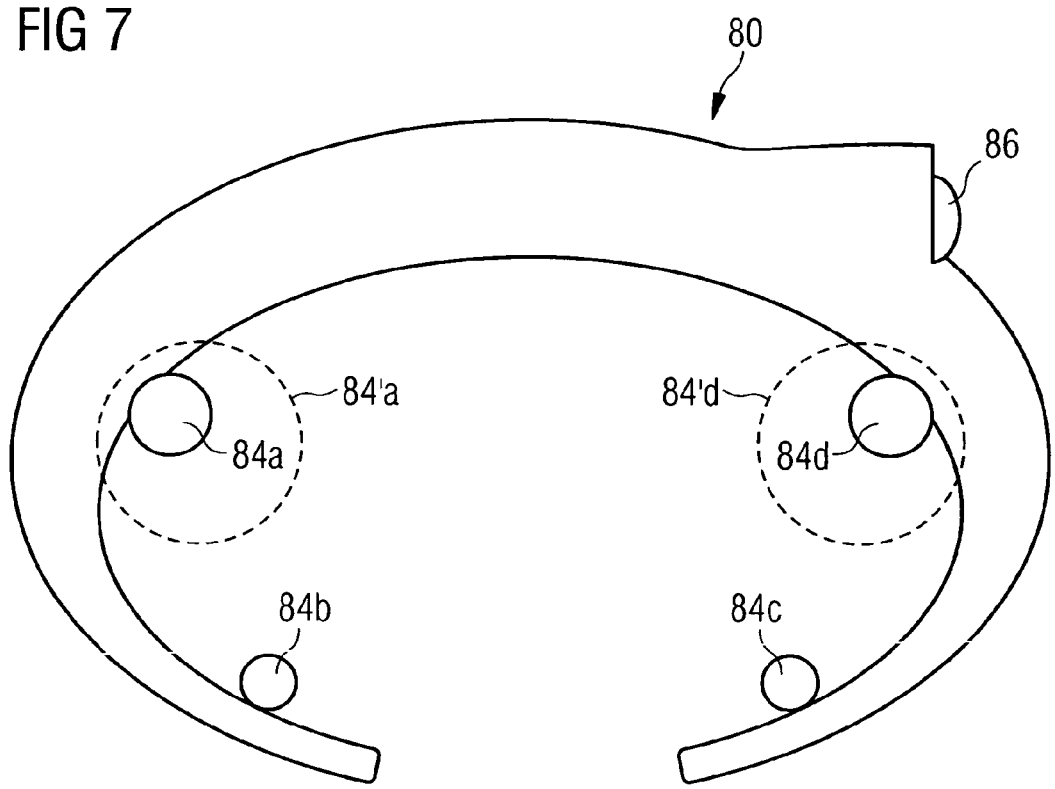
FIG. 7 shows the wireless mobile wearable device in a side view.

FIG. 7 shows the wireless mobile wearable device 80 in a side view. As show in FIGS. 5 and 6 the mobile device 80 comprises a camera system 86 as an exemplary sensing device 86. Additionally or alternatively the mobile device 80 can comprises another type of sensing device 86 such as a RFID reader, a barcode scanner and so on. The inducing devices 84a, 84d shown in FIG. 7 comprise inflatable and deflatable airbags 84a, 84d as exemplary inducing devices 84a, 84d. In an initial state the inducing devices 84a, 84d do not provide a pressure to the operator's skin. By inflating the airbags 84a, 84d by pressurized air the airbag increase their volumes to an actuated state of the inducing devices 84a', 84d' marked by dashed lines in FIG. 7. In that state the inducing devices 84a', 84d' can convey pressure on the skin of the operator. The mobile device can also comprise vibration motors 84b, 84c as exemplary inducing device 84b, 84c.

Figure 8:
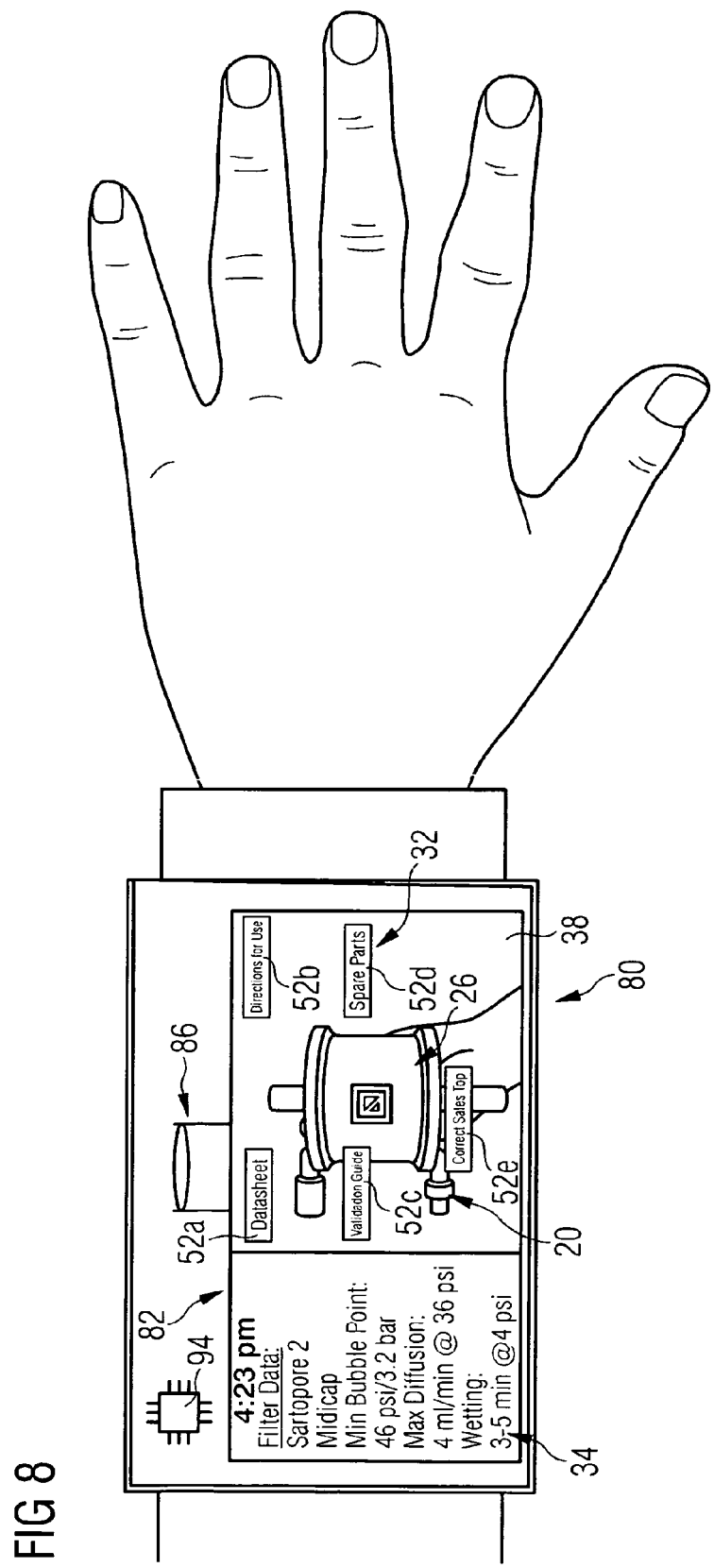
FIG. 8 shows a detailed view of a mobile display of the wireless mobile wearable device.

FIG. 8 shows a detailed view of the mobile display 82 of the wireless mobile wearable device 80. The mobile display 82 can be a touch screen display allowing the operator to make selections or input data via the mobile display 82. As shown the mobile display 82 can display an augmented display image 38 including the image data 36 captured by the camera 86, which shows a filter device 20 with a visual marker 26 allowing the mobile processing device 94 to identify the filter device 20, as well as additional information 34 about the filter device 20 and control elements 52a to 52e. This allows the operator to obtain all related and/or necessary information about a component, such as the filter device 20, before assembling this component to a set-up.

Figure 9A:
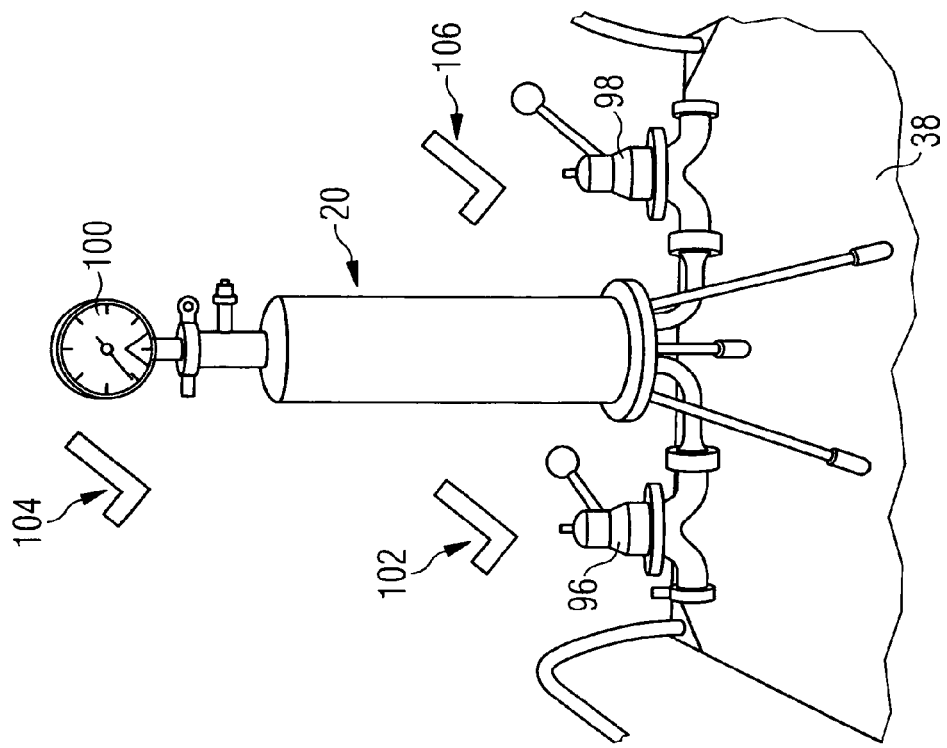
FIG. 9a shows an augmented image.
Figure 9B:
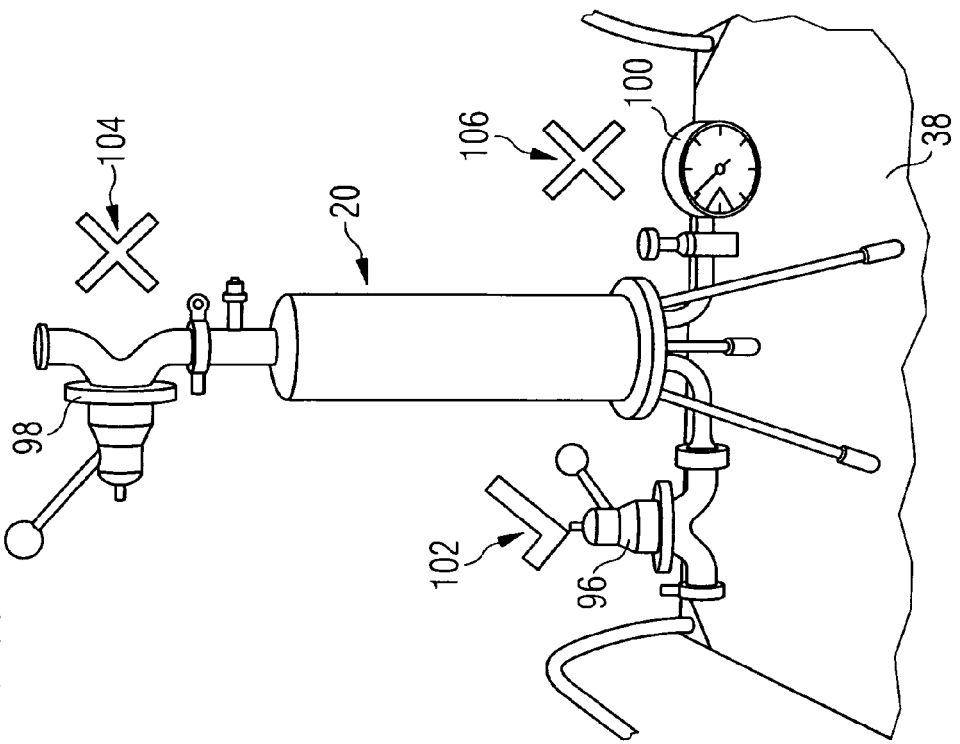
FIG. 9b shows another augmented image.

As shown in FIGS. 9a and 9b the augmented reality system 10 as previously shown in FIGS. 1 to 8 may also be sensitive to markers which are defined only by the shape and/or orientation of the respective components itself. FIG. 9a shows an augmented image 38 which can be displayed on a display device 18 or a mobile display device 82. The augmented image 38 comprises the representation of a filter device 20, a first valve 96, a second valve 98 and a manometer 100. All these components are identified based on their shape by the processing device 16. Based on the specification of the filter device 20 the processing device 16 comes to the decision, that the position of the manometer 100 and the second valve 98 is swapped with respect to the correct assembly, while the first valve is correctly assembled. Therefore, the augmented image 38 further comprises a first status indicator 102, which indicates the correct assembly of the first valve by means of a check mark and a second 104 and third 106 status indicator, which indicate the incorrect assembly of the second valve 98 and the manometer 100 by means of a cross.

Initiated by the operator the augmented image 38 may be enriched by data sheets or step-by-step instructions in order to solve the detected problem. After solution of the problem by correctly assembling all components as shown in FIG. 9b, the augmented image 38 shows the correct assembly of the second valve 98 and the manometer 100 together with the first to third status indicators 102, 104, 106.

FIG. 10 shows an augmented reality system 10 for testing the integrity or leak tightness of an integrity testable product 108, such as a disposable bag or bioreactor. The features of the augmented reality system 10 shown in FIG. 10 are analogous to the system shown in the previous figures and, thus, respective features are labeled with respective reference signs. The integrity testable product 108 comprises a fluid connector 110 and a product marker 112, such as a barcode or a pictograph, which can be recognized by a camera 14 of the augmented reality system 10. Alternatively or additionally the integrity testable product 108 can comprise an RFID tag readable by an RFID reader (not shown). The integrity testable product 108 is placed in a working space 12 between two product holders 114a, 114b each provided with a product holder marker 116a, 116b.

To perform the integrity test the fluid connector 110 of the integrity testable product 108 is connectable to a product connector 118 of a connection hose 24, wherein the product connector 118 comprises an connection hose marker 28 and the connection hose 24 is in fluid connection to an integrity testing device 22. The augmented reality system further comprises a processing device 16 operated by an augmented reality software and at least one display device 18, wherein the processing device 16 and the display device 18 can be part of the integrity testing device 22. The integrity testing device 22 can further comprise an integrity test device marker 29.

The integrity testing device 22 can be setup as a singular, multiple, remote, or a networked architecture of devices. A singular integrity testing device 22 can be placed at a fixed location or on a mobile cart and can provide data at the point of use or transmit data to networked and/or mobile devices. Multiple integrity testing devices can be placed in fixed and/or mobile positions throughout a facility and/or in multiple facilities. These multiple integrity testing devices can operate as singular units or as master/slave unit configurations and can provide data at the point of use or transmit data to networked and/or mobile devices. Networked integrity testing devices can be placed in fixed and/or mobile positions throughout a facility and/or in multiple facilities and can operate as a distributed network model of units, a master/slave network model of units, a network hub model of units, or a parallel processing model of units. Networked integrity testing devices can provide data at each point of use or transmit data to networked and/or mobile devices. A remote integrity testing device can be placed in a location separate from the integrity testing area and connected to the integrity testing device by tubing and/or piping lines. A remote integrity testing device can operate on all types of network configurations and provide data at each point of use or transmit data to networked and/or mobile devices.

Equipment such as a multi-valve connection device (not shown) can be connected to and controlled by the integrity testing device 22 or augmented reality system 10 to operate multiple integrity tests with a plurality of integrity testable products 108 from the same integrity testing device 22. The multi-valve connection device can be utilized to perform integrity and/or filterability testing on multiple integrity testable products 20, 108 in sequence where the operator can monitor, control, or receive real-time data at the point of use or from a networked and/or mobile device (80, as shown in FIGS. 5 to 8). The augmented reality system 10 can be integrated directly into the integrity testing device 22 and can operate in conjunction with the integrity testing device 22, operate as a supplemental system to the integrity testing device 22, operate as a networked system with the integrity testing device 22, or operate as a mobile networked device with the integrity testing device 22. The integrity testing device(s) 22 can connect directly to the processing device 16 and/or display device 18 or other at least one sensing devices 14 through wired or wireless connections.

The integrity testing by means of the integrity testing device 22 being in fluid connection with the integrity testable product 108 offers a non-destructive method for testing the product 108 when it is produced, prior to use, post-use, or when they are in-use or through conducting destructive testing on a representative number of samples to verify that the quality of a product is within specifications. The integrity testing device 22 can apply a pressurized fluid, such as sterile air, to the integrity testable product 108, such as a sterile bag or container. The pressurized fluid can be supplied through a fluid supply hose 25 to the integrity testing device 22 and from there to the integrity testable product 108. In case the leak tightness of the integrity testable product 108 is within predetermined limits measured applied pressure will not drop below a predetermined pressure value within a given time limit. In order to allow the application of a fluid pressure to an inflatable bag as exemplary integrity testable product 108 the volume increase of the inflatable bag is delimited by the product holders 114a, 114b to a predetermined amount.

Figure 11:
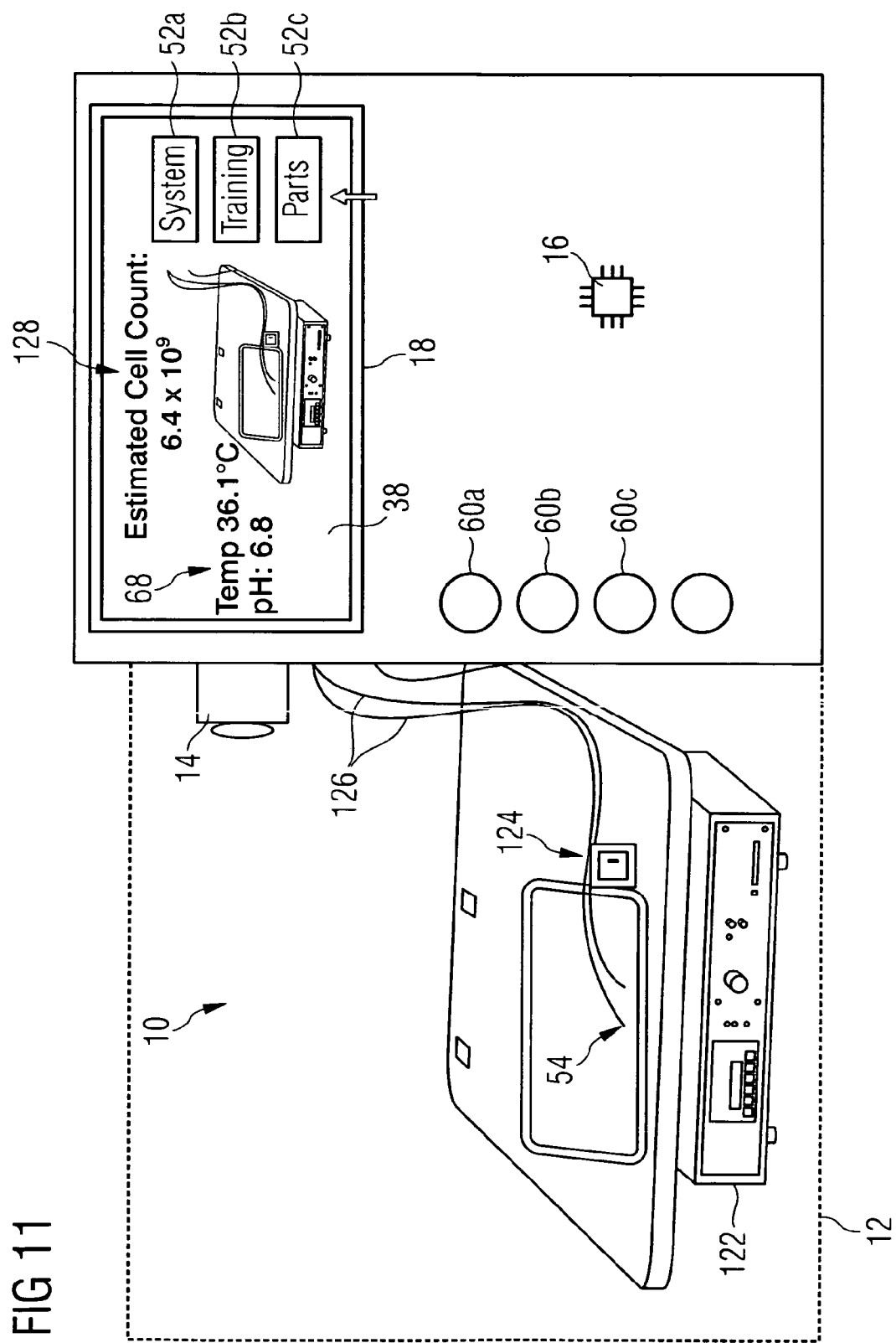
FIG. 11 shows an augmented reality system for operating an incubated container.

FIG. 11 shows an augmented reality system 10 for operating an incubated container 120 in a production set-up. An incubated container can be any one of a bioreactor, a disposable bioreactor, a fermentation tanks, a fermentation equipment, an incubator, a medical incubator, an animal/livestock incubator, an incubated shaker, a cell/virus culture vessel, a tissue culture vessel, another disposable incubated vessel or a combination of any of these incubated containers. The incubated container 120 is located on a container rocker system 122 within a working space 12. The rocker system 122 can be configured for an agitation of the incubated container 120, for heating or cooling the incubated container 120 and/or for capturing various parameters of the incubated container 120, such as its weight, temperature, and so on.

The augmented reality system comprises at least one sensing device 14, a processing device 16, an augmented reality software, and at least one display device 18. Further, the features described with respect to FIGS. 1 to 10 regarding capturing sensing data, recognizing markers from the captured data, displaying information, retrieving information from databases, and decision making based on the captured data and the retrieved information are also applicable to the augmented reality system 10 described in the following.

The at least one sensing device 14 is configured to detect at least one type of marker, such as an visual marker, an RFID tag and so on, that is embedded and/or mounted on a component of the production set-up in particular on the incubated container 120 in order to read a unique identification from the marker and/or localize the marker. At least one sensing device 14 can be a camera device 14 configured to capture optical markers, e.g. bar codes, color codes, pictograph, the shape of items, alphanumeric characters etc. As an example an incubated container marker 124 in form of a pictograph is attached to the incubated container 120, wherein a unique serial number may be encoded in an area of the incubated container marker 124.

The sensing devices can be located inside or outside of the incubated container 120. Sensing devices (not shown) located inside of the incubated container 120 can be protectively covered, shielded, or encased to provide protection of the respective sensing device from the environment, to prevent contamination of the sensing device from the environment, to prevent contamination of the environment by the sensing device, or to allow cleaning and/or sterilization of the surfaces of the sensing device. Sensing devices 14 located outside of the incubated containers can be configured for sensing at least one incubated container marker 124 located on or embedded into the incubated container 120, monitor changes of the incubated container 120 and/or within the incubated container 120. This may include visible or electronic sensing through glass, plastic, plexiglass, and/or transparent or opaque materials of the incubated container 120 or by electronic sensing through the incubated containers 120 walls.

The augmented reality system 10 may further comprise at least one associated sensor 54 located inside or near the incubated container 120. Associated sensors 54 can detect changes including, but not limited to, weight, volume, temperature, pH, dissolved oxygen, $CO_2$, and/or glucose levels. The data collected from these associated sensors 54 and processed by the processing device 16 or a mobile processing device 94 can be used to calculate values such as the predicted fill volume of a container based on weight and the known density of a filling material or to determine growth of organisms, such as plants, bacteria or other microorganisms. Manually conducted and entered cell counts and/or automated cell counts through flow cytometry or other process from samples of the media can be used or by calculations that uses information gathered from one or more of these sources can be utilized to calculate and/or estimate the number of cells present in the incubated container 120. Virus titers can be determined by RT-PCR based quantification, filter hybridization assays, manual and/or automated viral plaque assays or by calculating the number of infected or lysed cells inside the incubated container 120.

A representation of the growth or population numbers 128, a representation of the associated data 68 captured by the at least one associated sensor 54, an image of the incubated container 120 and/or at least one control element 52*a*, 52*b*, 52*c* can be superpositioned to an augmented display image, which can be displayed on the display device 18. The representation 128 of the growth number and/or the population number can be a static number, an estimated growth number updated at a certain interval, a growth curve or an estimated growth curve updated at a certain interval. In particular, the at least one sensing systems 14 ability to detect changes in the incubated container 120 over time can be utilized to determine growth of mammalian cells, bacteria, yeasts, molds, and/or viruses. A visual sensing system, such as a camera, can detect changes in the opaqueness and/or cloudiness of the media caused by growth or color changes of a media associated dye (cyanine or other dye). The data captured by the at least one associated sensor 54 can be transmitted via a wired connection 126 or via a wireless connection.

The at least one sensing device 14 and/or the at least one associated sensor 54 can be utilized for detecting possible contamination and/or undesired growth in an incubated container 120. This detection can include the visual detection of an out of specification color, e.g. by means of a color camera as an exemplary sensing device 14, when compared to previous cultures of growth (possibly mold and/or bacterial contamination) or changes to a specific dye indicator in the media. Associated sensors 54 can detect changes including, but not limited to, pH, dissolved oxygen, $CO_2$, and/or glucose levels to determine the alteration or changes in growth associated with a contaminant. Alterations in the calculated and/or estimated growth curve can be utilized to determine potential contamination inside of the incubated container 120. The operator can be alerted through an augmented display image 38 displayed on the display device 18 of the possible contamination of the incubated container.

The augmented reality system 10 can alert the user through an augmented display image and/or an acoustic signal and/or a haptic signal, if the processing device 16 discriminates a possible contamination, irregular growth curves, and/or out of specification data from associated sensors 54. The processing device 16 can automatically and/or manually run a systems check to diagnose or isolate the potential cause of the out of specification. The processing device 16 can further retrieve additional information from a local or remote database, for example to instruct the operator through a troubleshooting guide that can use an augmented display device 18 to guide the operator through potential causes of the out of specification, potential solutions to correct the problem, or methods to prevent the problem. The augmented reality system 10 can automatically and/or manually transmit the data associated with the out of specification to a technical support center for further troubleshooting. The response from or communication with the technical support center to troubleshoot and/or resolve the issue can be displayed as an augmented display image 38 on the display device 18.

The augmented reality system's 10 capability to detect the distance, the orientation and/or the movement of the incubated container marker and other markers related to components, such as the container rocker system 122 and the connection cable 126, relative to the at least one sensing device 14, can be used to determine if the components, e.g. equipment, devices, parts, materials, items, or consumables, are properly assembled for a desired measurement or production set-up. The decision whether the assembly is correct can be performed as described with respect to FIGS. 1 to 10.

Further, based on the recognized incubated container marker 124, the processing device 16 can retrieve additional information about the respective incubated container 120, such as control parameters for the measurement, experiment or production for which the incubated container 120 should be used. Therefore, the incubated container marker 124 can contain a unique identification such as a unique serial number in order to distinguish between two distinct incubated containers 120. In particular the processing device 16 can also act as an incubated container controlling device, which can control associated equipment, such as pumps 60*a*, valves 60*b*, heating or cooling devices 60*c*, the rocker device 122 and so on, according to the control parameters. For example, a heating device and/or an agitation device of the container rocker system 122 can be controlled by the processing device 16 in order to keep the temperature within the incubated container 120 within predetermined limits. A separate incubated container controlling device (not shown) can also be provided in order to control the measurement or production operation. Incubated container controlling device and/or processing device 16 together with the respective associated equipment 60*a*, 60*b*, 60*c* can be gathered together and/or named a container controlling unit.

Furthermore, the augmented reality system's 10 capability to detect the distance, the orientation and/or the movement of the incubated container marker and other markers related to components, such as the container rocker system 122 and the connection cable 126, relative to the at least one sensing device 14, can be used to recognize and track the movements of the respective markers 124 and/or physical movements of the operator to determine if proper technique of a pre-determined task is being followed within some set margin of error. The tracking of markers for performing or following proper technique of a predetermined task can be used in conjunction with a step-by-step training program, in which an operator is instructed, shown, and then evaluated for the performance of a set task via the display device 18. The operator can be evaluated and/or graded within an operator defined system for performing or following the proper technique for a pre-determined task within the margin of error by the software which tracks the movements of the markers and/or physical movements of the respective operator. The tracked movements of the markers and/or the operator can be recorded into a file while performing or following a pre-determined task or set of tasks for use as a template or master file for proper technique, for adding to other tasks to create a set of tasks, or for compiling and overlaying multiple prerecorded tasks to observe long term improvements in the technique of the operator or potential ergonomic improvements for the operator to make.

In medical, animal, or livestock incubated containers 120 the movements or activities of the subject(s) inside the incubated container 120 can be tracked, recorded, and/or compared with previous datasets. The information can be for example displayed as an augmented display image as a wireframe diagram of marker movements or calculated as a numerical value representing the activity of the subject(s). A physical marker can be placed on the internal/external body parts of the subjects or the external body parts can be used as a physical marker to track activity. The data associated with the tracked movements can be utilized to track health of the incubated subject, the responsiveness of the subject, sleep cycles and/or circadian rhythms. The data of tracked movements can also be used to recognize and alert the operator in an augmented display of the lack of movement, behaviors or symptoms of illness, injury, or death.

Figure 12:
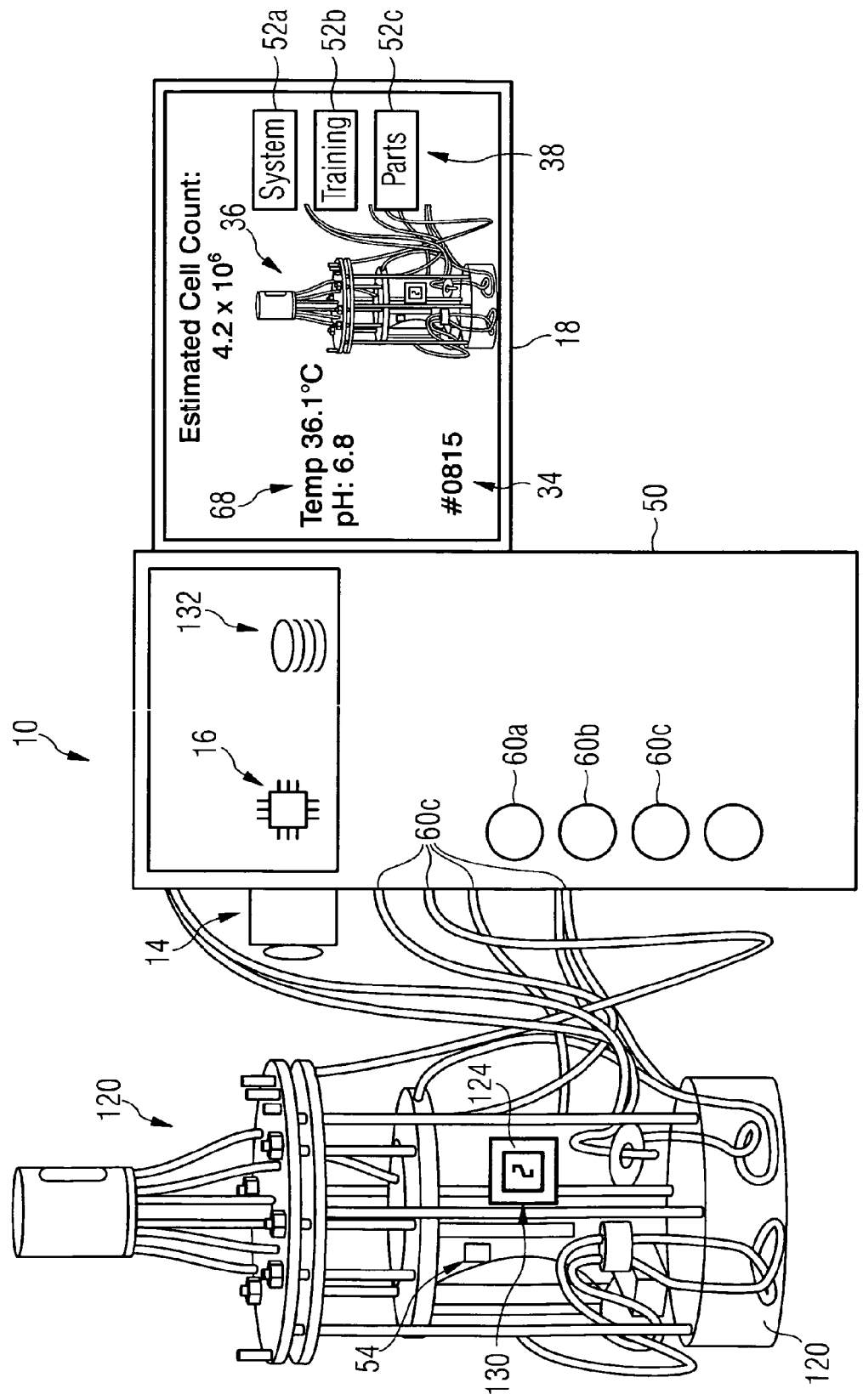
FIG. 12 shows an augmented reality system for operating a spinner flask.

FIG. 12 shows an augmented reality system 10 for operating a spinner flask 120 as exemplary incubated container 120 in an exemplary production set-up. The augmented reality system shown in FIG. 12 comprises within a housing 50 a camera 14 as exemplary sensing device 14, a processing device 16 operated by an augmented reality software, and a display device 18, such as an touch screen display 18. The housing 50 can also contain associated equipment, such as pumps 60a, valves 60b, and supply terminal 60c (e.g. for pressurized air, water, etc.), for controlling and/or supplying the incubated container during operation.

The sensing device can capture the unique identification from the incubated container marker 124 and match it with a dataset or file from a local and/or remote database, wherein additional information regarding the identified components can be retrieved and presented on the display device 18 within an augmented display image 38. The camera 14 can be setup in a fixed or movable position at the housing 50. Additional sensing devices may be located in the interior and/or exterior of the incubated container 120. Sensing devices in the interior of the incubated container 120 require protective coverings, shielding, or encasement to provide the equipment protection from the environment and allow cleaning or sterilization of the surfaces of the sensing device, such as sanitization with detergents or clean in place sterilization with heat or steam inside a bioreactor or fermenter container.

Sensing devices located outside of the incubated container 120 need to be positioned to view the working space 12. In case a sensing device should capture an optical image of at least part of the interior and/or the content of the incubated container 120, the respective sensing device has to view through a transparent barrier, such as a video camera setup to look through the glass or plastic of an incubated container 120. Alternatively, the respective sensing device has to be able to reliably detect signals through a barrier, as in the case of using an RFID reader and RFID tags as markers attached to tissue culture flasks in an incubator.

When the camera 14 captures and the processing device 16 recognizes an incubated container marker 124, the marker's unique identification can be matched with a local and/or remote database. At least a part of additional information 34 retrieved from the database can be presented on the display device 18 together with the image 36 captured by the camera 14.

Analogous to the system described with respect to FIG. 11 the augmented reality system 10 may further comprise at least one associated sensor 54 located inside or near the incubated container 120. Associated sensors 54 can detect changes in the physical and/or chemical parameters inside the incubated container 120, which may be caused by growth of organisms, such as plants, bacteria or other microorganisms. A representation of the associated data 68 captured by the at least one associated sensor 54 can be comprised by the augmented display image 38, which is displayed by the display device 18. Further, the captured data from the at least one associated sensor 54 can be saved into a local or remote database or saved to a storage medium 132. Furthermore, at least one control element 52a, 52b, 52c can be superpositioned to augmented display image 38. In case the display device 18 comprises a touch screen display, the touching of a control element 52a, 52b, 52c by an operator can be recognized, whereby predetermined tasks can be carried out, if the respective control element 52a, 52b or 52c is touched.

The incubated container marker 124 mounted to the incubated container 120 can comprise a marker display 130, such as a liquid crystal display (LCD), an electronic ink display, or light emitting diodes (LED), in order to display data belonging to the incubated container 120. The marker display 130 can be connected to at least one associated sensor 54 and can be configured to display at least one measurement value measured by means of the at least one associated sensor 54. The marker display 130 can for example continuously display the temperature and/or the pH value within the incubated container 120. The marker display 130 can also display an unique identification of the incubated container 120. The data displayed by the marker display 130 can be captured by the camera 14 of the augmented reality system 10 and can further be recognized by the processing device 16, for example by means of an optical character recognition software. The recognized data from the marker display 130 can be displayed as part of the augmented display image 38 by means of the display device 18. Further, the recognized data from the marker display 130 representing data from the at least associated sensor 54 located at or in the incubated container 120 can be saved into a local or remote database or saved to a storage medium 132, such as a hard disk, a floppy, a CD, a magneto-optical disk, a solid state memory, a FLASH memory, an USB memory stick, and so on.

Figure 13:
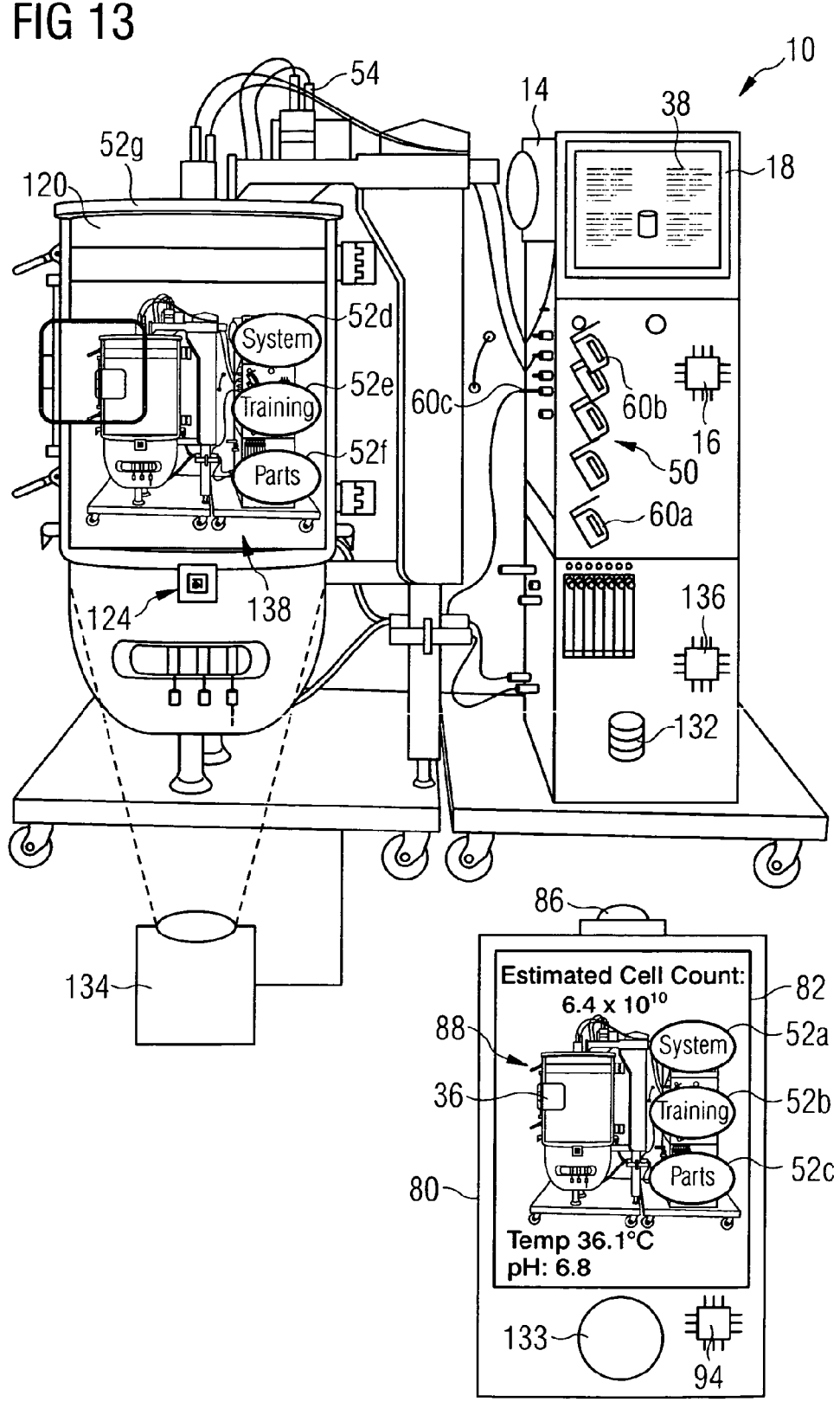
FIG. 13 shows an augmented reality system for operating a bioreactor.

FIG. 13 shows an augmented reality system 10 at a production set-up for operating a bioreactor 120 as exemplary incubated container 120 having an incubated container marker 124. The augmented reality system shown in FIG. 13 comprises within a housing 50, such as a moveable stainless steel housing, a camera 14 as exemplary sensing device 14, a processing device 16 operated by an augmented reality software. The housing 50 also contains associated equipment, such as pumps 60*a*, valves 60*b*, and supply terminal 60*c* (e.g. for pressurized air, water, etc.), for controlling and/or supplying the incubated container during operation. The augmented reality system 10 can also comprise associated sensors 54 capturing data, such as weight, temperature, pH value, moisture content, etc., from the incubated container 120. The associated sensors 54 can be connected by a wired or wireless connection to the processing device 16. As described in detail in view of FIG. 12, the associated sensors 54 can also be connected to a marker display of the incubated container marker 124 and the data captured by the associated sensors 54 may be transmitted via a marker display (not shown) and the camera 14 to the processing device 16. The augmented reality system 10 can also comprise an incubated container controlling device 136 for controlling the operation of the bioreactor 120. The incubated container controlling device 136 can for example control the operation of the associated equipment 60*a*, 60*b*, 60*c*. The control can be based on data and/or instructions from the processing device 16. The set-up and operation of the bioreactor 120 and the devices integrated in the housing 50 is analogous to the operation and set-up augmented reality system 10

The augmented reality system 10 further comprises at least one display device 18, 82, 134. A touch screen display 18 can be mounted to the housing 50. Additionally or alternatively to the mounted touch screen display 18, the augmented reality system 10 can comprise a mobile device 80 with a mobile display 82. The mobile device 80 can communicate in real-time by means of a wired or wireless connection with the processing device 16, e.g. in order to obtain data for displaying, and/or the incubated container controlling device 136, e.g. in order to transmit instructions to the incubated container controlling device 136. The mobile display 82 can be a monitor and/or touch screen visual display. Further, the mobile device 80 may comprise an acoustic device (not shown) for generating audio signals.

An augmented reality software can run on a processing device 94 of the mobile device 80 in order to display an augmented reality image 88 on the mobile display device 82, which can be substantially identical to the augmented display image 38 displayed on the display device 18. As shown in FIG. 13. superposed to the captured image data 36 the augmented reality image 88 on the mobile display device 82 comprises a representation of the associated data 68 captured by the at least one associated sensor 54 as well as at least one control element 52*a*, 52*b*, 52*c*. By actuating the touch screen display 82 at an area showing one of the at least one control elements 52*a*, 52*b*, 52*c* a respective predetermined task can be initiated. The predetermined task can be related to a retrieval of additional information from a local or remote database and the display of the retrieved additional information. Further, the predetermined task can comprise the transmission of a control instructions to the processing device 16 and/or the incubated container controlling device 136, e.g. for controlling the heating, cooling and/or the agitation of the incubated container 120 or for initiating the execution of a measurement by the at least one associated sensors 54.

Additionally to the camera 14 or for replacement of the camera 14 the mobile device 80 can comprise at least one mobile sensing device 86, for example the mobile camera 86. Camera 86 may be a digital still camera or a digital video camera. The mobile camera 86 can replace the camera 14 mounted to the housing 50, wherein the mobile camera 86 provide image data to the mobile processing device 94. The mobile processing device 94 can recognize the markers, such as the incubated container marker 124, contained in the image data. Additional information linked to recognized markers and retrieved from a local and/or remote database can be displayed within an augmented reality image 88 analogous to the mobile device described conferring to FIGS. 5 to 8. Thus, the mobile device 80 can provide the same functionality as mobile device described with respect to FIGS. 5 to 8.

In an embodiment the augmented reality system 10 for operating the incubated container 120 comprises associated equipment, such as pumps 60*a*, valves 60*b*, and supply terminal 60*c* controlled by an incubated container controlling device 136. The associated sensors 54 can be connected by a wired or wireless connection also to the incubated container controlling device 136 or to a processing device 16. The incubated container controlling device 136 and/or to the processing device 16 can be connected to a storage medium 132 such as an internal hard disk drive or a solid state memory device in order to record at least a part of the data captured during the operation of the incubated container 120. The incubated container controlling device 136 and/or to the processing device 16 is connected to a mobile device 80, for example by a wireless connection, such as a WLAN connection, to a wireless mobile device 80. The mobile device 80 comprises at least one mobile sensing device 86, such as a mobile camera 86. The mobile camera 86 can capture image data depending on the field of view and the direction of the mobile camera. Provided that the mobile camera 86 is directed to a working space containing the incubated container 120, the mobile camera 86 can capture images of the incubated container 120 and transmit these images to the mobile processing device 94. The mobile processing device 94 can recognize the markers, such as the incubated container marker 124, contained in the image data and retrieve related additional information from a local and/or remote database. A local database can be stored on a storage medium 133 of the mobile device 80 such as an internal hard disk drive or a solid state memory device. A connection to the remote database can be established by an WLAN connection, a cell phone connection or a bluetooth connection. The remote database can also be located on the storage medium 132 connected to the processing device 16 and/or the incubated container controlling device 136. Further, the augmented reality system 10 can be fully and/or solely controllable via the mobile device 80, thus, preventing unauthorized operations by an unauthorized user having access to the incubated container 120 or other associated equipment, but not having access to the mobile device 80. Alternatively, the augmented reality system 10 can be operated via the mobile device 80 using the mobile processing device 94 to provide a user with an augmented display image 38 without an unauthorized user having access to the incubated container 120, other equipment, or other associated equipment 60. The mobile device 80 can be for example a cell phone, a smart phone, a netbook, a notebook, a tablet computer, an electronic reader, or the like.

The augmented reality system 10 can additionally or alternatively to the touch screen device 18 and/or the mobile display device 82 comprise a display projector device 134, such as a beamer or the like, that projects an augmented projected image 138 to a projection area. The projection area can comprise the face and/or surface of the incubated container 120, a floor, a ceiling and/or a wall of the working space where the incubated container 120 is located. The position, origin and/or size of the projection area can be defined by a marker such as the incubated container marker 124. In particular the incubated container marker 124 can comprise a reflecting area, such as a white label area, on which the augmented projected image 138 can be projected. The augmented projected image 138 can also appear to a recipient as an overlay to the incubated container marker 124.

The augmented projected image 138 can be generated in accordance with the spatial distribution, such as the position and/or orientation, of the projection area. In case the projection area is turned with respect to the display projector device 134 for example, so that a trapezoidal distorted picture is projected on the projection area, the augmented projected image 138 can be rectified by applying a keystone correction to the original image in order to obtain a rectified image on the turned projection area. The quality of the keystone correction can be controlled by capturing an augmented projected image 138 containing an element known in shape by means of a camera 14, 86, wherein the captured element contained in the captured augmented projected image 138 is compared to the known element. The keystone correction can be continuously adapted in order to obtain a minimum derivation between the known element and the captured element.

The augmented projected image 138 can also contain at least one control element 52*d*, 52*e*, 52*f*, which can be superposed to the augmented projected image 138.

The occlusion of one of at least one of the control elements 52*d*, 52*e*, 52*f* can be recognized analogous to the recognition of a marker. The augmented projected image 138 can be captured for example by the camera 14. In case the operator is occluding one control elements 52*d*, 52*e*, 52*f* with an occluder, such like a finger or other body part, the processing device 16 processing the image data captured by the camera 14 can recognize, which of the control elements 52*d*, 52*e*, 52*f* is occluded. Depending on the occluded control element 52*d*, 52*e*, 52*f* a predetermined task can be initiated.

The augmented projected image 138 can be utilized in multiple ways to assist the operator in obtaining information or for performing tasks related to the incubated container 120, for example by displaying of information about components, equipment, parts, consumables or items located inside and/or attached to the incubated container 120 can be achieved by selecting the appropriate control element 52*d*, 52*e*, 52*f*. This achieved information can be intuitively linked to the component in question by generating an according augmented projected image 138, wherein the desired information is displayed near or onto the component in question. The control of the augmented reality system 10 by using the occlusion of control elements can prevent the touching of components or a display device 18, which might already be contaminated or which may be contaminated by chemicals and/or microorganisms attached to the operator's hand or glove. Further, the use of an occluder allows additional information to be easily accessed without requiring the operator to physically input the information by taking their hands out of a barrier system to touch a touch screen, a keyboard or mouse to initiate a task.

As an alternative or additional to control elements 52*d*, 52*e*, 52*f*, which are part of an augmented projected image 138, also physical markers, such as barcodes, pictographs attached to a component or characteristic shapes or elements of a component, such as a screw, an engraving, and so on, can be used as a control element. For example the rim 52*g* of the incubated container 120 can be used as an exemplary control element 52*g*. Touching or occluding this rim 52*g* by the operators hand can be captured by the camera 14 and recognized by the processing device 16, wherein a recognition of this occlusion can initiate a predefined task, such like starting the display projector device 134 in order to generate the augmented projected image 138 on the surface of the incubated container 120.

FIGS. 14*a* to 14*c* show possible arrangements of a plurality of control elements 52, which can be presented on the display device 18 as a virtual marker or projected by a display projector device as described with reference to FIG. 13. Alternatively, the control elements 52 can be painted or printed on a surface, such as the surface of a component or the floor, the ceiling or any wall of the working space. The occlusion of any one of the control elements 52 can be captured and recognized by a camera and a processing device as described before. The control elements can form a virtual keyboard 140 following an ergonomically layout, as shown in FIG. 14*a*, following an V-shape layout, as shown in FIG. 14*b*, or following a linear layout, as shown in FIG. 14*c*. By occluding the control elements 52 of the virtual keyboard 140 an operator can input arbitrary information to the system, for example to the processing device. This input of information can include, but not limited to, letters, numbers, symbols or text or issue an electronic command to send data to a device or piece of equipment, a software program, or to enter in a predetermined set of data.

As shown in FIG. 15 different types of components 144*a* to 144*h* can be represented by different assigned pictograph markers. By identifying the different markers the augmented reality system can obtain information regarding the type and purpose of the respective component of the measurement or production set-up. Occluding the respective marker, for example by the operator's hand, can initiate a predefined action. Power switch marker 142*a* can be assigned to a power switch 144*a* switching on or off the whole system. Agitator marker 142*b* can be assigned to an agitator 144*b*, whereby occluding the agitator marker 142*b* can switch on or off the agitator 144*b*. Fermentation tank marker 142*c* can be assigned to an incubated container 144*c*, wherein occluding marker 142*c* can initiate the display of belonging additional information or status data, e.g. temperature, pH value, etc., via a display device. Valve marker 142*d* can be assigned to a valve 144*d*, whereby occluding the valve marker 142*d* can open or close the valve 144*d*. Pump marker 142*e* can be assigned to a pump 144*e*, whereby occluding the pump marker 142*c* can switch on or off the pump 144*e*. Filter marker 142*f* can be assigned to a filter system 144*f*, whereby occluding the filter marker 142*f* can switch on or off the filtration by means of the filter system 144*f*. Bioprocess tank marker 142*g* can be assigned to a bioprocess tank 144*g*, wherein occluding marker 142*g* can initiate the display of belonging additional information or status data of the tank 144*g*. Emergency marker 142*h* can be assigned to an emergency stop switch 144*h*, whereby occluding the emergency marker 142*h* can shut down the whole system.

FIG. 16 shows a camera device 14 having a working space in its field of view, wherein a leakage occurs at the connection between a first connection hose 24 having a first connection hose marker 28 and a second connection hose 24*b* having a second connection hose marker 28*b*. A gas 146 and a liquid 148 are leaking at the connection of both hoses. The discharged gas 146 may be detected by a gas detector 54*i*, as an optional associated sensor, whereas the dripping liquid may be detected by a liquid indicator 54*j*, as an optional associated sensor. However, an unacceptable amount of liquid may be discharged from the leak before the liquid indicator 54*j* is reached and can indicate the presence of the leakage. A fluid pressure gauge 54*k*, as an optional associated sensor, can be provided in order to determine a pressure loss within the connection hoses. However, dripping leakage may cause only minor pressure loss.

In case the leak tightness of the integrity testable product 108 is within predetermined limits measured applied pressure will not drop below a predetermined pressure value within a given time limit. In order to allow the application of a fluid pressure to an inflatable bag as exemplary integrity testable product 108 the volume increase of the inflatable bag is delimited by the product holders 114a, 114b to a predetermined amount.

The camera 14 can capture a time series of images of the viewed working space. By a comparison of two images of the time series a change between the two images can be recognized, which is caused by leaking liquid, such as a leaking droplet. The presence and the location of the leaking can be discriminated, whereby an augmented image can be generated and displayed emphasizing the difference between the images. An operator can easily recognize to position and the amount of leakage and perform appropriate actions.

The invention claimed is:

1. An assembling method for assembling a measurement or production set-up comprising the steps:
   providing an augmented reality system with a processing device, an output device and at least one sensing device, whereby the at least one sensing device is capable of capturing sensing data belonging to a working space;
   providing a first set-up component having at least one first marker at the working space;
   providing a second set-up component having at least one second marker at the working space, wherein the second set-up component is connectable to the first set-up component;
   capturing the first marker and the second marker by the at least one sensing device;
   identifying the first and second marker, whereby the processing device retrieves respective digital information assigned to the identified first marker and second marker from a database and whereby the processing device makes a decision on the compatibility of the first set-up component with the second set-up component based on the retrieved digital information;
   outputting an augmented representation of at least part of the captured sensing data and the decision on the compatibility.

2. An assembling method according to claim 1, wherein the first set-up component is an integrity testing device or a container controlling unit.

3. An assembling method according to claim 1, wherein the second set-up component is any one of an integrity testable product, a container, a disposable container, a disposable bag, a bioreactor, a disposable bioreactor, a spinner flask, a filter device, a pump, a valve, a hose, and a supply terminal.

4. An assembling method according to claim 1, comprising the step:
   generating an enabling instruction in case the first set-up component is compatible to the second set-up component.

5. An assembling method according to claim 1, comprising the steps:
   determining the spatial distance between the first marker and the second marker based on the sensing data captured by the at least on sensing device, wherein the processing device makes a decision on a correct connection of the first set-up component with the second set-up component based on the determined spatial distance;
   output an augmented representation comprising a representation of the decision on the correct connection.

6. An assembling method according to claim 1, comprising the steps:
   determining the location of a component to be assembled by an operator;
   display the location of the component to the operator.

7. An operating method for operating a measurement or production set-up comprising the steps:
   providing an augmented reality system with a processing device, an output device and at least one sensing device, whereby the at least one sensing device is capable of capturing sensing data belonging to a working space;
   providing a first set-up component with a first marker at the working space;
   capturing the first marker by the at least one sensing device;
   identifying the first marker, whereby the processing device retrieves digital information assigned to the identified first marker from a database and whereby the processing device provides a set of instructions for performing the measurement or production using the first set-up component based on the retrieved digital information;
   outputting an augmented representation of at least part of the captured sensing data and at least part of the retrieved digital information;
   performing the measurement or production operation according to the set of instructions;
   providing a second set-up component connectable to the first set-up component;
   capturing a second marker of the second set-up component by the at least one sensing device;
   identifying the second marker, whereby the processing device retrieves digital information assigned to the identified second marker from a database and whereby the processing device makes a decision on the compatibility of the first set-up component with the second set-up component based on the retrieved digital information;
   outputting an augmented representation of at least part of the captured sensing data and the decision on the compatibility;
   performing the measurement or production in case the first set-up component is compatible with the second set-up component.

8. An operating method according to claim 7, wherein the first set-up component is any one of an integrity testing device, a container controlling unit, a hose, a pump, a valve, a tank, a piping, an integrity testable product, a container, and an incubated container, such as a bioreactor, a disposable bioreactor, a fermentation tank, a fermentation equipment, an incubator, a medical incubator, an animal/livestock incubator, an incubated shaker, a cell/virus culture vessel, a tissue culture vessel, a disposable incubated vessel, or a disposable bag.

9. An operating method according to of claim 7, wherein the first set-up component is monitored by the at least one sensing device during the measurement or production operation, wherein the processing device generates an alert notice if the monitored data deviates from expected data beyond a predetermined variation, wherein the expected data and/or the tolerable variation is retrieved from the database.

10. An operating method according to claim 9, wherein the monitored data is recorded to a database.

11. An operating method according to claim 7, wherein the second set-up component is an integrity testing device or a container controlling unit and wherein the operating method comprises the step:
   sending an enabling instruction to the integrity testing device or to the container controlling unit in case the first set-up component is compatible to the second set-up component.

12. An operating method according to claim 7, wherein the operating method further comprises the steps:
   determining the spatial distance between the first marker and the second marker based on the sensing data captured by the at least one sensing device, wherein the processing device makes a decision on a correct connection of the first set-up component with the second set-up component based on the determined spatial distance;

outputting an augmented representation comprising a representation of the decision on the correct connection.

13. An operating method for operating a measurement or production set-up comprising the steps:
    providing an augmented reality system with a processing device, an output device and at least one sensing device, whereby the at least one sensing device is capable of capturing sensing data belonging to a working space;
    providing a first set-up component with a first marker at the working space;
    capturing the first marker by the at least one sensing device;
    identifying the first marker, whereby the processing device retrieves digital information assigned to the identified first marker from a database and whereby the processing device provides a set of instructions for performing the measurement or production using the first set-up component based on the retrieved digital information;
    outputting an augmented representation of at least part of the captured sensing data and at least part of the retrieved digital information;
    performing the measurement or production operation according to the set of instructions;
    capturing a time series of images of the working space comprising at least the first set-up component;
    comparing at least two images of the time series of images;
    determining a change between the at least two images;
    outputting a message in case a change between the at least two images occur near the first set-up component.

14. A testing method for testing the integrity of an integrity testable product comprising the steps:
    providing an augmented reality system with a processing device, an output device and at least one sensing device, whereby the at least one sensing device is capable of capturing sensing data belonging to a working space;
    providing an integrity testable product with at least one product marker at the working space;
    providing at least one test set-up component connectable to the integrity testable product;
    capturing the product marker by the at least one sensing device;
    identifying the product marker, whereby the processing device retrieves digital information assigned to the identified product marker from a database and whereby the processing device makes a decision on the compatibility of the integrity testable product with the test setup component based on the retrieved digital information;
    outputting an augmented representation of at least part of the captured sensing data and the decision on the compatibility;
    performing the integrity test in case the integrity testable product is compatible with the test setup component.

15. A testing method according to claim 14, wherein one of the at least one test setup component is an integrity testing device and wherein the testing method further comprises the step:
    sending an enabling instruction to the integrity testing device in case the at least one testing setup component is compatible to the integrity testable product.

16. Augmented reality system for operating a measurement or production set-up, the augmented reality system comprising:
    at least one sensing device capable of capturing sensing data belonging to a working space;
    a processing device, which is in communicatively connected to the at least one sensing device, and which is capable of
        detecting the presence of a first marker of a first set-up component in the sensing data captured by the at least one sensing device,
        identifying the first marker,
        retrieving a digital information assigned to the identified first marker, and
        making a decision on the compatibility of the first set-up component with a second set-up component based on the retrieved digital information and/or operating the measurement or production set-up according to a set of instructions contained in the retrieved digital information;
    an output device for outputting an augmented representation of at least part of the captured sensing data as well as the decision on the compatibility and/or at least a part of the retrieved digital information.

17. Augmented reality system according to claim 16, wherein at least one sensing device is a camera, preferably a mobile camera.

18. Augmented reality system according to claim 16, further comprising an integrity testing device or a container controlling unit.

19. Augmented reality system according to claim 16, wherein the output device is a projector projecting the augmented representation onto the working space or onto a set-up component, whereby the augmented representation is adjusted and displayed in accordance with the spatial distribution of the component.

20. Augmented reality system according to claim 16, wherein the at least one sensing device and the output device is part of a mobile device.

21. Augmented reality system according to claim 20, wherein the processing device is part of the mobile device.

22. Augmented reality system according to claim 20, wherein the mobile device is connected to an integrity testing device or a container controlling unit of the system via a wireless connection.

23. A computer program product for a computer-aided assembly of a measurement or production set-up and/or for automatically operating a measurement or production set-up, wherein the computer program product comprises coding segments that when loaded and executed on a suitable system can execute an operating method according to claim 1.

* * * * *